US012531162B1

(12) United States Patent
Vanaja

(10) Patent No.: US 12,531,162 B1
(45) Date of Patent: Jan. 20, 2026

(54) MULTI-DIMENSIONAL PHENOTYPIC SPACE FOR GENOTYPE TO PHENOTYPE MAPPING AND INTELLIGENT DESIGN OF CANCER DRUG THERAPIES USING A DEEP LEARNING NET

(71) Applicant: Northeastern University, Boston, MA (US)

(72) Inventor: Kiran Vanaja, Portland, ME (US)

(73) Assignee: Northeastern University, Boston, MA (US)

( * ) Notice: Subject to any disclaimer, the term of this patent is extended or adjusted under 35 U.S.C. 154(b) by 41 days.

(21) Appl. No.: 18/680,204

(22) Filed: May 31, 2024

Related U.S. Application Data

(60) Provisional application No. 63/610,097, filed on Dec. 14, 2023, provisional application No. 63/535,642, filed on Aug. 31, 2023, provisional application No. 63/470,056, filed on May 31, 2023.

(51) Int. Cl.

| | |
|---|---|
| ***G16H 70/00*** | (2018.01) |
| ***G16B 20/00*** | (2019.01) |
| ***G16B 40/20*** | (2019.01) |
| ***G16H 50/20*** | (2018.01) |
| ***G16H 70/40*** | (2018.01) |

(52) U.S. Cl.
CPC ............. *G16H 70/40* (2018.01); *G16B 20/00* (2019.02); *G16B 40/20* (2019.02); *G16H 50/20* (2018.01)

(58) Field of Classification Search
CPC ........ G16H 70/40; G16H 50/20; G16B 20/00; G16B 40/20
See application file for complete search history.

(56) References Cited

U.S. PATENT DOCUMENTS

| | | | | |
|---|---|---|---|---|
| 6,410,014 B1 * | 6/2002 | Seed | A61K 35/13 | 435/372.3 |
| 6,428,953 B1 * | 8/2002 | Naldini | C12N 7/00 | 435/456 |
| 6,475,769 B1 * | 11/2002 | Wilson | C12N 15/86 | 435/235.1 |
| 6,489,458 B2 * | 12/2002 | Hackett | C12N 15/90 | 435/445 |
| 6,534,055 B1 * | 3/2003 | June | C07K 14/70521 | 435/375 |
| 6,537,540 B1 * | 3/2003 | Burstein | A61P 19/02 | 435/456 |
| 6,537,594 B1 * | 3/2003 | Paoletti | C07K 14/33 | 435/69.51 |

(Continued)

OTHER PUBLICATIONS

Andrés-Galiana, Elsevier, 2019, pp. 1-8.*

(Continued)

*Primary Examiner* — Michael I Ezewoko
(74) *Attorney, Agent, or Firm* — Foley Hoag LLP; Dana M. Gordon; Lee Chedister

(57) ABSTRACT

Systems and methods are disclosed for mapping single-cell 'omics data in a phenotypic space. The method comprises reading single-cell 'omics data; providing the single-cell 'omics data to a trained artificial neural network, the trained artificial neural network mapping the single-cell 'omics data to a point in a phenotypic space; determining a trajectory of the point within the phenotypic space based on at least one drug therapy; and classifying an efficacy of the at least one drug therapy based on the trajectory.

15 Claims, 22 Drawing Sheets

(56) References Cited

U.S. PATENT DOCUMENTS 6,569,457 B2 * 5/2003 Ullah ................. A61K 31/7048 424/475
6,638,534 B1 * 10/2003 Ishibashi .............. A61K 9/5078 424/494
6,682,743 B2 * 1/2004 Mayr ................... A61K 39/285 435/235.1
6,713,068 B1 * 3/2004 Audonnet .............. A61K 39/39 435/5
6,753,162 B1 * 6/2004 Seed ...................... A61K 40/31 435/69.1
6,761,893 B2 * 7/2004 Chaplin .................. A61P 31/20 435/235.1
6,780,407 B1 * 8/2004 Paoletti .............. C07K 14/5434 435/320.1
6,780,417 B2 * 8/2004 Kaslow ................ C07K 14/445 435/69.3
6,793,926 B1 * 9/2004 Rasty ..................... C12N 15/86 435/235.1
6,797,514 B2 * 9/2004 Berenson ........... C07K 16/2803 436/526
6,821,515 B1 * 11/2004 Cleland ................... A61P 35/00 424/138.1
6,867,041 B2 * 3/2005 Berenson ........... C07K 16/2833 436/526
6,869,794 B2 * 3/2005 Vogels ................... C12N 7/025 435/235.1
6,887,466 B2 * 5/2005 June ................... C07K 16/2833 435/375
6,893,865 B1 * 5/2005 Lockert .................... C12N 7/00 424/94.4
6,905,680 B2 * 6/2005 June ................... C07K 16/2812 435/375
6,905,681 B1 * 6/2005 June ..................... C07K 16/289 435/375
6,905,874 B2 * 6/2005 Berenson ........... C07K 16/2875 436/526
6,913,752 B2 * 7/2005 Chaplin ................. A61K 39/12 435/235.1
6,913,922 B1 * 7/2005 Bout ...................... C12N 15/86 435/456
6,923,973 B1 * 8/2005 Cox ................... A61K 39/0002 424/274.1
6,924,128 B2 * 8/2005 Allen ....................... C12N 7/00 435/456
6,936,466 B2 * 8/2005 Feldhaus ................ C12N 15/86 435/235.1
6,943,019 B2 * 9/2005 Wilson ................... C12N 15/86 435/235.1
6,953,690 B1 * 10/2005 Gao ................... A61K 48/0091 435/456
6,955,808 B2 * 10/2005 Curiel .................... C12N 15/86 435/456
6,974,695 B2 * 12/2005 Vogels ................. C12N 15/861 435/235.1
6,991,797 B2 * 1/2006 Andersen ............... A61K 39/04 424/234.1
7,029,848 B2 * 4/2006 Vogels ................... C12N 15/86 435/235.1
7,045,313 B1 * 5/2006 Moss ................... A61K 39/275 435/235.1
7,097,842 B2 * 8/2006 Suter ...................... C12N 15/86 435/235.1
7,115,391 B1 * 10/2006 Chen ...................... C12N 15/86 435/456
7,144,575 B2 * 12/2006 June ................. C07K 14/70532 435/375
7,148,203 B2 * 12/2006 Hackett ................. C12N 15/90 536/23.4
7,160,682 B2 * 1/2007 Hackett .................... C12N 9/22 536/23.4
7,172,893 B2 * 2/2007 Rabinowitz ............. A61P 21/04 435/235.1
7,175,843 B2 * 2/2007 June ................... C07K 16/2896 435/375
7,189,536 B2 * 3/2007 Chaplin .................. A61P 31/14 435/235.1
7,198,784 B2 * 4/2007 Kingsman .......... A61K 48/0091 435/325
7,232,566 B2 * 6/2007 June ..................... C07K 16/289 435/375
7,255,862 B1 * 8/2007 Tartaglia .............. C07K 14/005 424/188.1
7,259,015 B2 * 8/2007 Kingsman ............... A61P 25/16 435/456
7,283,337 B2 * 10/2007 Sakai ................... G11B 5/3932 360/324.12
7,303,910 B2 * 12/2007 Bebbington ......... C07K 14/005 435/320.1
7,335,364 B2 * 2/2008 Chaplin ............... C07K 14/005 435/235.1
7,351,585 B2 * 4/2008 Mitrophanous ........ C12N 15/86 435/325
7,384,644 B2 * 6/2008 Chaplin .................. A61P 31/12 435/237
7,445,924 B2 * 11/2008 Chaplin ................. A61K 39/12 435/239
7,459,270 B2 * 12/2008 Chaplin .................. A61P 43/00 435/235.1
7,529,685 B2 * 5/2009 Davies .................... G16Z 99/00 707/999.005
7,572,631 B2 * 8/2009 Berenson ............... A61K 40/42 435/375
7,608,279 B2 * 10/2009 Parisot .................... A61P 31/10 424/283.1
7,628,980 B2 * 12/2009 Suter .................... A61K 38/212 435/235.1
7,705,120 B2 * 4/2010 Lillie ................... C12Q 1/6886 536/23.4
7,708,949 B2 * 5/2010 Stone ...................... B01F 25/45 422/68.1
7,741,465 B1 * 6/2010 Eshhar ................... C07K 16/32 435/325
7,767,449 B1 * 8/2010 Paoletti ................ C07K 14/005 435/235.1
7,892,533 B2 * 2/2011 Suter .................... A61K 38/215 435/235.1
7,897,156 B2 * 3/2011 Ackermann ............ A61P 37/04 424/281.1
7,923,017 B2 * 4/2011 Chaplin ................... C12N 7/00 435/235.1
7,939,086 B2 * 5/2011 Chaplin .................. A61P 35/00 435/235.1
7,964,395 B2 * 6/2011 Chaplin ................. A61K 39/12 435/235.1
7,964,396 B2 * 6/2011 Chaplin ................. C12N 15/86 435/235.1
7,964,398 B2 * 6/2011 Chaplin ................. A61K 39/12 435/235.1
7,985,739 B2 * 7/2011 Kay ........................ C12N 9/22 435/320.1
8,034,334 B2 * 10/2011 Dudley ............. A61K 39/0011 435/372.3
8,088,379 B2 * 1/2012 Robbins ............... G01N 33/505 435/7.1
8,163,293 B2 * 4/2012 Chaplin .................. A61P 35/00 424/199.1
8,211,422 B2 * 7/2012 Eshhar ............... A61K 40/4205 514/44 R
8,227,432 B2 * 7/2012 Hackett .................... C12N 9/22 536/23.1
8,236,560 B2 * 8/2012 Chaplin ............... C07K 14/005 435/235.1
8,268,325 B2 * 9/2012 Chaplin ............... C07K 14/005 424/199.1
8,268,329 B2 * 9/2012 Chaplin .................. A61P 35/00 435/5
8,278,036 B2 * 10/2012 Kariko ........... C12Y 305/04004 435/375

(56) References Cited

U.S. PATENT DOCUMENTS

| | | | | |
|---|---|---|---|---|
| 8,309,098 | B2 * | 11/2012 | Howley | A61P 31/18; 424/199.1 |
| 8,372,622 | B2 * | 2/2013 | Suter | A61K 38/212; 435/235.1 |
| 8,392,127 | B2 * | 3/2013 | Watters | C12Q 1/6886; 435/6.13 |
| 8,399,645 | B2 * | 3/2013 | Campana | A61P 35/00; 536/23.4 |
| 8,404,658 | B2 * | 3/2013 | Hajjar | A61P 9/00; 514/44 A |
| 8,454,972 | B2 * | 6/2013 | Nabel | A61P 37/04; 424/202.1 |
| 8,470,598 | B2 * | 6/2013 | Chaplin | A61K 39/12; 435/235.1 |
| 8,557,779 | B2 * | 10/2013 | Sugiyama | A61K 40/4243; 514/19.3 |
| 8,589,175 | B2 * | 11/2013 | Glauser | G16H 50/50; 600/300 |
| 8,697,854 | B2 * | 4/2014 | Schendel | C12N 15/85; 536/23.5 |
| 8,796,414 | B2 * | 8/2014 | Johnston | A61P 35/00; 530/300 |
| 8,843,356 | B2 * | 9/2014 | Schadt | G16B 25/10; 703/11 |
| 8,906,682 | B2 * | 12/2014 | June | C12N 7/00; 435/372.3 |
| 8,911,993 | B2 * | 12/2014 | June | C12N 7/00; 435/372.3 |
| 8,916,381 | B1 * | 12/2014 | June | A61K 40/11; 435/372.3 |
| 8,975,071 | B1 * | 3/2015 | June | C07K 16/2803; 435/372.3 |
| 9,101,584 | B2 * | 8/2015 | June | A61K 48/005 |
| 9,102,760 | B2 * | 8/2015 | June | A61P 35/00 |
| 9,102,761 | B2 * | 8/2015 | June | A61P 43/00 |
| 9,115,402 | B2 * | 8/2015 | Hacohen | G01N 33/6878 |
| 9,342,657 | B2 * | 5/2016 | Wei | G16H 50/70 |
| 9,556,237 | B2 * | 1/2017 | Schmaljohn | C07K 14/175 |
| 9,909,159 | B2 * | 3/2018 | Marras | C12Q 1/686 |
| 9,962,453 | B2 * | 5/2018 | Georges | A61P 31/00 |
| 10,144,927 | B2 * | 12/2018 | Kampmann | C12N 15/111 |
| 10,185,803 | B2 * | 1/2019 | Frey | G16B 20/20 |
| 10,202,640 | B2 * | 2/2019 | Davis | C12Q 1/686 |
| 10,249,389 | B2 * | 4/2019 | Athey | A61K 31/37 |
| 10,360,499 | B2 * | 7/2019 | Kumar | G16B 40/20 |
| 10,395,772 | B1 * | 8/2019 | Lucas | G16H 10/60 |
| 10,426,824 | B1 * | 10/2019 | Hacohen | A61K 40/42 |
| 10,553,318 | B2 * | 2/2020 | Athey | G06N 3/08 |
| 10,665,326 | B2 * | 5/2020 | Aliper | G16B 40/30 |
| 10,801,070 | B2 * | 10/2020 | Clement | G16B 30/00 |
| 10,975,442 | B2 * | 4/2021 | Hacohen | G01N 33/57407 |
| 11,087,460 | B2 * | 8/2021 | Buckler | G06F 18/24 |
| 11,164,082 | B2 * | 11/2021 | Kumar | G06V 10/82 |
| 11,321,327 | B2 * | 5/2022 | Stennett | G06F 16/24568 |
| 11,403,316 | B2 * | 8/2022 | Lee | G16H 70/20 |
| 11,410,763 | B2 * | 8/2022 | Frieder | G06N 7/01 |
| 11,424,008 | B2 * | 8/2022 | Lee | G06N 3/088 |
| 11,436,246 | B2 * | 9/2022 | Lee | G16B 5/00 |
| 11,452,768 | B2 * | 9/2022 | Hacohen | C07K 16/2803 |
| 11,640,859 | B2 * | 5/2023 | Colley | G16H 20/00; 702/19 |
| 11,705,226 | B2 * | 7/2023 | Colley | G16B 40/00; 705/3 |
| 11,725,237 | B2 * | 8/2023 | Shukla | G16B 20/00; 702/19 |
| 11,834,718 | B2 * | 12/2023 | Clement | G16B 30/00 |
| 11,869,664 | B2 * | 1/2024 | Frieder | G06N 7/01 |
| 11,887,696 | B2 * | 1/2024 | Frey | G06N 3/04 |
| 11,939,637 | B2 * | 3/2024 | Hacohen | C12Q 1/6886 |
| 11,967,400 | B2 * | 4/2024 | Lee | G16C 20/70 |
| 12,009,061 | B2 * | 6/2024 | Peters | G16B 40/20 |
| 12,073,561 | B2 * | 8/2024 | Buckler | G06V 20/69 |
| 12,087,404 | B2 * | 9/2024 | Lee | G16H 70/60 |
| 12,112,839 | B2 * | 10/2024 | Colley | G16H 20/10 |
| 12,125,572 | B2 * | 10/2024 | Buckler | G16B 5/00 |
| 12,131,472 | B2 * | 10/2024 | Buckler | G06V 10/82 |
| 12,141,975 | B2 * | 11/2024 | Buckler | G06T 3/00 |
| 12,159,406 | B2 * | 12/2024 | Buckler | G06F 18/2148 |
| 12,211,623 | B2 * | 1/2025 | Frieder | G06F 18/24 |
| 12,229,957 | B2 * | 2/2025 | Buckler | G06T 3/00 |
| 12,236,595 | B2 * | 2/2025 | Buckler | G06F 18/211 |
| 12,260,939 | B2 * | 3/2025 | Garcia | G16B 25/10 |
| 12,336,804 | B2 * | 6/2025 | Narayan | A61B 5/068 |
| 12,383,196 | B2 * | 8/2025 | Etkin | A61B 5/377 |
| 12,394,524 | B2 * | 8/2025 | Ng | G06N 3/08 |
| 2003/0046114 | A1 * | 3/2003 | Davies | G16Z 99/00; 705/3 |
| 2003/0104008 | A1 * | 6/2003 | Loosmore | C07K 14/005; 424/199.1 |
| 2004/0013648 | A1 * | 1/2004 | Kingsman | A61P 25/28; 435/235.1 |
| 2004/0053304 | A1 * | 3/2004 | Markowitz | A61P 35/00; 435/325 |
| 2006/0008468 | A1 * | 1/2006 | Chiang | A61K 39/001184; 424/193.1 |
| 2006/0163385 | A1 * | 7/2006 | Link | B01F 25/45; 239/423 |
| 2006/0252077 | A1 * | 11/2006 | Buzby | C12Q 1/6869; 435/6.12 |
| 2006/0258607 | A1 * | 11/2006 | Jarosch | A61P 3/04; 435/6.16 |
| 2007/0003442 | A1 * | 1/2007 | Link | B01F 25/45211; 422/400 |
| 2007/0025970 | A1 * | 2/2007 | Kingsman | A61P 25/16; 435/456 |
| 2007/0055049 | A1 * | 3/2007 | Grey | C07K 14/70539; 530/350 |
| 2007/0083334 | A1 * | 4/2007 | Mintz | G16B 40/00; 702/19 |
| 2007/0134197 | A1 * | 6/2007 | Eichner | A61P 37/04; 424/85.7 |
| 2007/0143149 | A1 * | 6/2007 | Buttner | G16H 10/60; 705/3 |
| 2007/0184489 | A1 * | 8/2007 | Griffiths | B01L 3/502761; 435/7.1 |
| 2007/0195127 | A1 * | 8/2007 | Ahn | G01N 15/1404; 347/55 |
| 2008/0003142 | A1 * | 1/2008 | Link | B01L 3/565; 264/219 |
| 2008/0014222 | A1 * | 1/2008 | Simmons | A61K 40/11; 424/277.1 |
| 2008/0254008 | A1 * | 10/2008 | Dropulic | A61K 39/12; 435/5 |
| 2009/0005254 | A1 * | 1/2009 | Griffiths | B01J 19/0046; 506/7 |
| 2009/0026082 | A1 * | 1/2009 | Rothberg | G01N 27/414; 422/400 |
| 2009/0055944 | A1 * | 2/2009 | Korman | A61P 1/16; 424/1.49 |
| 2009/0111106 | A1 * | 4/2009 | Mitrophanous | A61P 25/16; 435/235.1 |
| 2009/0131543 | A1 * | 5/2009 | Weitz | B82Y 30/00; 366/177.1 |
| 2009/0136494 | A1 * | 5/2009 | Ponath | A61P 1/04; 424/133.1 |
| 2009/0186042 | A1 * | 7/2009 | Johnston | A61P 35/00; 530/387.9 |
| 2009/0220980 | A1 * | 9/2009 | Hoon | C12Q 1/6886; 435/6.12 |
| 2010/0137143 | A1 * | 6/2010 | Rothberg | G01N 27/4145; 506/38 |
| 2010/0137163 | A1 * | 6/2010 | Link | C12Q 1/6876; 506/40 |
| 2010/0158951 | A1 * | 6/2010 | Randolph | A61P 37/04; 424/278.1 |
| 2010/0203531 | A1 * | 8/2010 | Sarkaria | C12Q 1/6886; 435/6.12 |
| 2010/0210529 | A1 * | 8/2010 | van der Burg | A61P 35/00; 514/19.3 |

(56) References Cited

U.S. PATENT DOCUMENTS

2010/0282617 A1* 11/2010 Rothberg ............... H10D 30/68 205/780.5
2010/0297071 A1* 11/2010 Ishibashi ................ A61P 35/00 424/85.5
2010/0304989 A1* 12/2010 Von Hoff ............... G16H 50/20 506/9
2011/0015869 A1* 1/2011 Watters .................. G16B 40/20 702/19
2011/0097312 A1* 4/2011 Molldrem .......... A61K 40/4247 424/277.1
2011/0257890 A1* 10/2011 Weinschenk ....... G01N 33/6878 702/19
2011/0293571 A1* 12/2011 Widdowson ............ A61P 25/08 435/320.1
2011/0293637 A1* 12/2011 Hacohen .......... A61K 39/39558 424/277.1
2012/0004893 A1* 1/2012 Vaidyanathan ........ G16H 50/50 703/11
2012/0082691 A1* 4/2012 Rammensee .. A61K 39/001193 424/185.1
2012/0219947 A1* 8/2012 Yurkovetsky ........... B01F 25/14 435/6.11
2012/0244133 A1* 9/2012 Rosenberg ............. A61P 35/00 435/372
2012/0288539 A1* 11/2012 Eber ........................ A61K 9/10 514/21.1
2012/0295960 A1* 11/2012 Palfi ....................... C12N 15/86 514/44 R
2013/0071414 A1* 3/2013 Dotti ...................... C12N 15/86 435/320.1
2013/0210014 A1* 8/2013 Sharman .............. C12Q 1/6886 435/6.12
2013/0295110 A1* 11/2013 Binder ........... A61K 39/001194 424/277.1
2014/0056986 A1* 2/2014 Desai ...................... A61P 35/00 424/491
2014/0178438 A1* 6/2014 Sahin ...................... A61P 37/04 424/277.1
2014/0256595 A1* 9/2014 Link ....................... C40B 60/08 506/16
2014/0322716 A1* 10/2014 Robins ................. C12Q 1/6881 435/6.12
2014/0365242 A1* 12/2014 Neff ....................... G16H 10/60 707/756
2015/0072893 A1* 3/2015 Kampmann ....... C12N 15/1075 506/10
2015/0140041 A1* 5/2015 Vitiello ................ C12Q 1/6874 424/277.1
2015/0224182 A1* 8/2015 Hunt .............. A61K 39/001156 435/325
2015/0324527 A1* 11/2015 Siegel .................... G16B 50/30 705/3
2016/0008447 A1* 1/2016 Hacohen ................ G16B 15/00 424/174.1
2016/0101170 A1* 4/2016 Hacohen ................ A61K 40/19 424/277.1
2016/0213771 A1* 7/2016 Sampson ............. A61K 38/164
2016/0306917 A1* 10/2016 Wei ...................... A61K 31/555
2016/0310584 A1* 10/2016 Fritsch ................... A61K 47/26
2016/0326593 A1* 11/2016 Clement ................ G16B 30/10
2016/0331822 A1* 11/2016 Hacohen .......... A61K 39/39558
2016/0339090 A1* 11/2016 Hacohen ............ C07K 16/2803
2017/0160269 A1* 6/2017 Linnemann .......... G01N 33/505
2017/0233821 A1* 8/2017 Lianidou .............. C12Q 1/6858 435/6.11
2017/0298441 A1* 10/2017 Wu ...................... C12Q 1/6858
2018/0000913 A1* 1/2018 Hacohen ............ G01N 33/5011
2018/0039726 A1* 2/2018 Boissel .................... G16B 5/00
2018/0055922 A1* 3/2018 Hacohen .......... A61K 39/39558
2018/0108440 A1* 4/2018 Stevens .................. G06N 3/044
2018/0127803 A1* 5/2018 Lei .......................... C12Q 1/68
2018/0153975 A1* 6/2018 Fritsch ........... A61K 39/001152
2018/0330824 A1* 11/2018 Athey .................... G16B 40/00
2019/0050534 A1* 2/2019 Apte ...................... C12Q 1/689
2019/0060428 A1* 2/2019 Fritsch .................... A61P 37/02
2019/0060432 A1* 2/2019 Hacohen ................. A61P 43/00
2019/0096526 A1* 3/2019 Hirsch ................ G06F 21/6245
2019/0099475 A1* 4/2019 Benz .................... C12N 5/0638
2019/0376147 A1* 12/2019 Fritsch ................. C12Q 1/6858
2020/0004751 A1* 1/2020 Stennett ............ G06F 16/24568
2020/0016251 A1* 1/2020 Hacohen ................ G16B 15/00
2020/0069783 A1* 3/2020 Hacohen .......... G01N 33/57492
2020/0258601 A1* 8/2020 Lau ........................ G16H 50/20
2020/0330571 A1* 10/2020 Fritsch ........... A61K 39/001191
2021/0090694 A1* 3/2021 Colley ................... G16B 30/00
2021/0233664 A1* 7/2021 Colley ................... G16H 50/70
2021/0366577 A1* 11/2021 Koller .................... G06N 3/045
2022/0157403 A1* 5/2022 Mason ................... G06N 5/022
2022/0165359 A1* 5/2022 Lee ........................ G06N 3/045
2022/0262462 A1* 8/2022 Peters .................... G16B 20/00
2022/0307026 A1* 9/2022 Senapathy ............. G16B 45/00
2022/0310196 A1* 9/2022 Polykovskiy .......... G16B 20/00
2022/0310198 A1* 9/2022 Collins .................. G16B 35/20
2022/0310201 A1* 9/2022 Senapathy ............. G16H 20/10
2022/0310274 A1* 9/2022 Senapathy ............. G16H 15/00
2022/0310275 A1* 9/2022 Senapathy ............. G16B 45/00
2022/0316009 A1* 10/2022 Senapathy ............. G16B 30/00
2022/0375611 A1* 11/2022 Gates .................. H04L 63/1441
2023/0122305 A1* 4/2023 Senapathy ............. G16B 20/10 435/6.11
2023/0148855 A1* 5/2023 Wang .................... G06T 7/0016 382/128
2023/0154567 A1* 5/2023 Senapathy ............. G16B 30/10 702/20
2023/0154580 A1* 5/2023 Wang ....................... A61B 1/31 382/118
2023/0170057 A1* 6/2023 Kozloski .................. G06N 3/08 702/19
2023/0223121 A1* 7/2023 Colley ................... G16B 30/00 705/2
2023/0245788 A1* 8/2023 Colley ................... G16H 20/00 702/19
2023/0368915 A1* 11/2023 Abraham ............. G01N 33/574
2023/0420143 A1* 12/2023 Buckler ................. G16H 50/50
2024/0112752 A1* 4/2024 Patwardhan ........... G16B 50/10
2024/0161017 A1* 5/2024 Pisner .................... G16H 50/20
2024/0194299 A1* 6/2024 Garcia ................... G16B 40/20
2024/0289586 A1* 8/2024 Balakrishnan ......... G06N 3/098
2024/0303544 A1* 9/2024 Baranzini .............. G06N 5/022
2024/0312581 A1* 9/2024 Colley ................... G16H 20/10
2024/0344138 A1* 10/2024 Benjamin .......... A61K 39/0011
2024/0404640 A1* 12/2024 Schaffer ................. G16B 40/20
2025/0125054 A1* 4/2025 Muhammad ........... G16B 20/00
2025/0182848 A1* 6/2025 Catterson ................. G06N 3/08
2025/0186406 A1* 6/2025 Zarrinpar ............. A61K 31/436
2025/0210196 A1* 6/2025 Frieder ................... G06F 9/545

OTHER PUBLICATIONS

Auwerx, HGG Advances, 2022, pp. 1-24.*
Azizi, CellPress, 2018 pp. 1293-1308.*
Chalancon, 2012, 2012 pp. 21-32.*
Dijik, CellPress, 2018, pp. 716-729.*
Herholt, Elsevier, 2020, pp. 18-35.*
Huang, CellPress, pp. 1-29.*
Kapoor, 2016, Elsevier, pp. 3232-3245.*
Karaca, 2018, Genetics in Medicine, pp. 28-37.*
Kashyap, CellPress, 2022, pp. 647-676.*
Knight, CellPress, 2022, pp. 916-938.*
Kriete, Computational Systems Biology, 2010, Chapter 14.*
Lee, Elsevier, 2017, pp. 118-123.*
Li, Elsevier, 2022, pp. 1-20.*
Lötsch, Elsevier, 2013, pp. 21-28.*
Masoudi-Sobhanzadeh, Elsevier, 2019, pp. 254-262.*
Nickel, Elsevier, 2015, pp. 126-142.*
Parisi, Elsevier, 2020, pp. 1043-1055.*
Perera, 2010, Elsevier, Chapter 22.*
Prasad, Elsevier, 2022, Chapter 21.*

(56) References Cited

OTHER PUBLICATIONS

Razo-Mejia, CellPress, 2018, pp. 56-69.*
Schirle, Elsevier, 2016, pp. 82-89.*
She, Elsevier, 2018, pp. 478-490.*
Sina, CellPress, 2019, pp. 955-966.*
Smart, CellPress, Feb. 2023, pp. 1-23.*
Tan, Elsevier, Jan. 2023, pp. 61-75.*
Vukoviv, Elsevier, 2018, pp. 58-66.*
Wellenreuther, CellPress, 2016, pp. 155-164.*
Wilard & Ginsburg, Genomic-and-Personalized-Medicine, Elsevier, 2009, Chapter 3.*
Wooten, Elsevier, 2017, 167-175.*
Xu, Elsevier, 2021, pp. 1-9.*
Zabinsky, Elsevier, 2019, pp. 21-35.*
Zitnik__Elsevier_2028_pp._71_91.*
Gómez-Echavarría, Elsevier, 2020, pp. 1081-1093.*

* cited by examiner

100

400

401 Input Layer
(17014 features)

|

402 Hidden Layer 1
(64 neurons, ReLU activation, L2 Regularization with lambda = 0.001)

|

403 Dropout Layer
(Dropout rate = 0.5)

|

404 Hidden Layer 2
(32 neurons, ReLU activation, L2 Regularization with lambda = 0.001)

|

405 Dropout Layer
(Dropout rate = 0.5)

|

406 Output Layer
(10 neurons, Linear activation (regression))

FIG. 4

MULTI-DIMENSIONAL PHENOTYPIC SPACE FOR GENOTYPE TO PHENOTYPE MAPPING AND INTELLIGENT DESIGN OF CANCER DRUG THERAPIES USING A DEEP LEARNING NET

RELATED APPLICATIONS

This application claims the benefit of priority to U.S. Provisional App. No. 63/470,056, filed May 31, 2023; U.S. Provisional App. No. 63/535,642, filed Aug. 31, 2023; and U.S. Provisional App. No. 63/610,097, filed Dec. 14, 2023; each of which are incorporated herein by reference in their entirety.

BACKGROUND OF THE DISCLOSURE

Cancer remains a stubbornly difficult disease to cure. While cancers with different origins and having multiple different mutations are often treated with specific inhibitors, the selective advantage of unregulated growth gained in the cancers is often the characteristic to be targeted. Complex diseases like cancer, which often have multiple driver mutations, are refractory to single therapeutic agent treatment. For combination therapies there are no rational, quantitative methods of design; instead, most combination drugs are heuristic, qualitative and are based on assumed additive effect.

There is a need to ensure that the trajectory that the cells traverse during therapy are away from phenotypes like stem cell, mesenchymal, survival, or autophagy which could contribute to resistance to therapeutics and drugs.

SUMMARY

According to certain aspects of the present disclosure, systems and methods are disclosed for mapping single cell ’omics data to a phenotypic space.

In one embodiment, a method comprises reading single-cell ’omics data; providing the single-cell ’omics data to a trained artificial neural network, the trained artificial neural network mapping the single-cell ’omics data to a point in a phenotypic space; determining a trajectory of the point within the phenotypic space based on at least one drug therapy; classifying an efficacy of the at least one drug therapy based on the trajectory.

In some embodiments, the trained artificial neural network comprises a feedforward neural network.

In some embodiments, the artificial neural network is pretrained by reading a genetic sequence; providing the genetic sequence to the artificial neural network; providing a collection of phenotypic measurements to the artificial neural network, and applying the collection of phenotypic measurements to a series of cell lines to populate a dataset; determining, from the populated dataset, an output vector representing each phenotype associated with the genetic sequence to thereby create a map of phenotypic measurements.

In some embodiment, the phenotypic space is defined by a plurality of phenotypic measurements.

In some embodiments, the method further comprises projecting a heterogenous group of cells into the phenotypic space.

In some embodiments, the method further comprises outputting a likelihood of survival based on a trajectory of the heterogeneous group of cells.

In some embodiments, the efficacy is based on one of apoptosis, migration, or autophagy.

In some embodiments, the method further comprises optimization of the phenotypic space based on known phenotypic effect of a cell treatment.

In some embodiments, the method further comprises outputting a set of phenotypic values characterizing the cell.

In some embodiments, single cell ’omics data comprises data on genomic alterations, DNA methylation sites, open chromatin sites, and mRNA or protein abundance.

In some embodiments, the trained artificial neural network comprises at least a preprocessing workflow.

In some embodiments, the preprocessing workflow comprises a windowing application.

In some embodiments, the preprocessing workflow further comprises a short-time Fourier transformation (STFT), the STFT transforming windowed single-cell ’omics sequencing data into a frequency domain.

In some embodiments, the method further comprises analyzing the frequency domain to recognize one or more patterns and/or to reduce noise.

In some embodiments, an output of the preprocessing workflow comprises an image pool for the single-cell ’omics sequencing data.

In some embodiments, the image pool comprises a spectrographic image.

In some embodiments, providing the single-cell ’omics sequencing data to a trained artificial neural network comprises an image input of the single-cell ’omics sequencing data.

In some embodiments, the method further comprises outputting an average pool of the phenotypic measurement and the phenotypic space; and predicting, based on the average pool, an associated combination of trajectories.

In an alternative embodiment, a system comprises a computing node comprising a computer readable storage medium having program instructions embodied therewith, the program instructions executable by a processor of the computing node to cause the processor to perform a method comprising reading a genetic sequence including single-cell ’omics sequencing data; providing the single-cell ’omics sequencing data to a trained artificial neural network, the trained artificial neural network mapping the genetic single-cell ’omics data to a phenotypic measurement and creating a phenotypic space for the genetic sequence; outputting the phenotypic measurement and the phenotypic space; classifying a trajectory of the phenotypic measurement in the phenotypic space within a likelihood of survival.

In an alternative embodiment, a computer program product comprises a computer readable storage medium having program instructions embodied therewith, the program instructions executable by a processor to cause the processor to perform a method comprising reading a genetic sequence including single-cell ’omics sequencing data; providing the single-cell ’omics sequencing data to a trained artificial neural network, the trained artificial neural network mapping the genetic single-cell ’omics data to a phenotypic measurement and creating a phenotypic space for the genetic sequence; outputting the phenotypic measurement and the phenotypic space; classifying a trajectory of the phenotypic measurement in the phenotypic space within a likelihood of survival.

BRIEF DESCRIPTION OF THE DRAWINGS

The accompanying drawings, which are incorporated into and constitute a part of this specification, illustrate various exemplary embodiments and together with the description, serve to explain the principles of the disclosed embodiments.

FIG. 4 is a schematic illustrating a feedforward neural network, in accordance with one or more embodiments of this disclosure.

DETAILED DESCRIPTION

Figure 1:
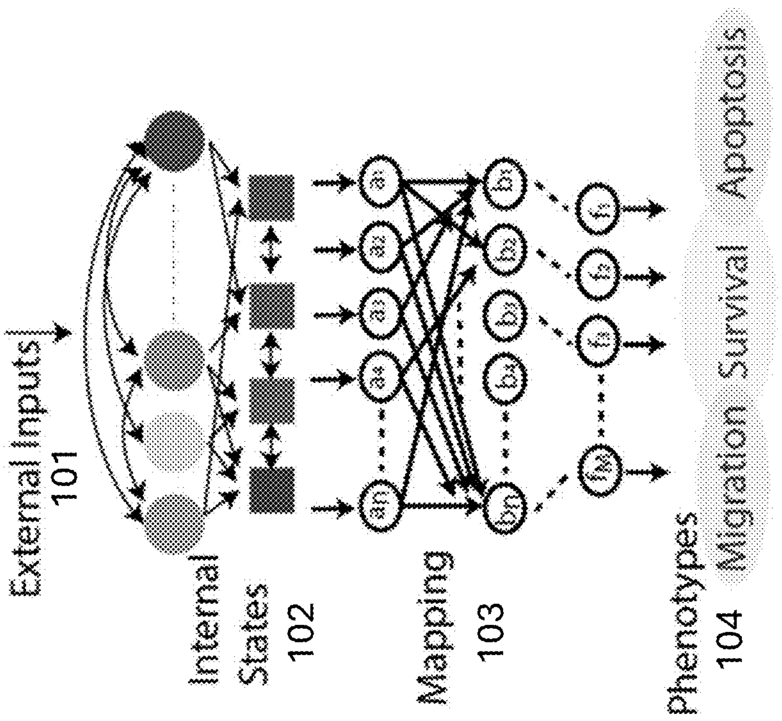
FIG. 1 is an integrated view of cell behavior, and mapping of internal states to phenotypes, in accordance with one or more embodiments of this disclosure.

Reference will now be made in detail to the exemplary embodiments of the present disclosure, examples of which are illustrated in the accompanying drawings. Wherever possible, the same reference numbers will be used throughout the drawings to refer to the same or like parts.

The systems, devices, and methods disclosed herein are described in detail by way of examples and with reference to the figures. The examples discussed herein are examples only and are provided to assist in the explanation of the apparatuses, devices, systems, and methods described herein. None of the features or components shown in the drawings or discussed below should be taken as mandatory for any specific implementation of any of these devices, systems, or methods unless specifically designated as mandatory.

Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

As used herein, the term “exemplary” is used in the sense of “example,” rather than “ideal.” Moreover, the terms “a” and “an” herein do not denote a limitation of quantity, but rather denote the presence of one or more of the referenced items.

Cancer has remained an incurable disease that afflicts all of humanity. Single agent therapy in conventional cancer treatments although results in initial tumor disappearance and resolution, resistance and recurrence occur in a majority of the cases. Combination therapies leverage the ability to target multiple different nodes of the same pathways or adjacent pathways that enable resistance. While the motivation is clear, the complexities of cancer signaling networks and the myriad small molecule drugs developed in previous decades make combination therapy design an intractable problem with most combination therapies designed on heuristics and presumed synergy. Increased knowledge and appreciation of factors that lead to heterogeneity like race, ethnicity, sex etc. make personalized approaches for therapy an urgent unmet need. Personalizing the combination therapy is an additional dimension to be optimized along with the rational combination therapy design.

While research and development in terms of diagnoses, treatment, cure and rehabilitation of various cancers have achieved unprecedented levels of innovation, progress and advancement, the best hope for a positive outcome is early detection followed by subsequent surgeries and therapies. Unfortunately, while a significant proportion of the primary tumors and cancers can be completely eliminated and caused to disappear by standard methods of treatment like surgeries, chemotherapies, precision therapies and their combinations, the recurrence rates and/or loss of remission remains disconsolately high. For example, after prostatectomy, the average recurrence rate of aggressive prostate cancer at 5 years is about 40%, after cystectomy the rate of return of bladder cancer is 50%, in glioblastoma, it is 100%, and in breast cancers, recurrence averages 30%. The loss of remission is a deterministically fatal event accompanied by secondary mutations, metastasis and a distinctly severe disease both in its onset and rapid progression. An often neglected and less spoken about condition in cancer disease treatment is mental health, including fear and stigma associated and attached with the metastatic disease. Patients in remission often suffer severe trauma wondering about the chance of recurrence; the associated fear of loss of remission is no doubt debilitating in nature. Although the 5 year in-remission mark is often considered a necessary threshold for curative signature, the constant fear of a disease recurrence, coupled with yearly pre-emptive scans, is a mental and physical burden that all cancer survivors face. We propose that an approach towards better outcomes for cancer treatment will focus on cancer treatments that are designed to minimize the chances of emergence of metastatic properties in cancers and/or recurrence of the more aggressive forms of cancers.

Cancer cells, the functional unit of a cancer, generate and derive a growth advantage by hijacking a pathway that often intersects directly with proliferation and growth. For example, tumors in the EGFR pathway, PI3K/Akt/mTOR pathway, RAS/RAF/MAPK pathway, Cyclins/CDK pathway, Rb/p53/PTEN/cMyc all directly influence the proliferation and growth of the cancer cells possessing these mutations. The gold standard treatment strategy for these cancers have been the inhibition of the mutations and subsequently the pathways that drive the cancers. Although in the short term this seems like a prescient approach, resistance and subsequent re-wiring of cellular networks have been the consequences in the long-term. A billion years of evolution of life on this planet have entrained the cellular pathways that regulate growth and proliferation with multiple redundancies to overcome the effects of attenuated signaling with mechanisms like feedback loops. This implies that attempting to block the effects of a driver mutation by a single therapeutic drug could easily trigger resistance by co-opting the available redundancies and mechanisms to restore signaling in cells driving recurrence and metastasis. Some of these redundancies and mechanisms include developing parallel adjoining phenotypic properties like survival, migration, autophagy, stemness, metabolic reprogramming and mesenchymal phenotype to name a few. Thus, the motivation for this proposal is to develop a tool to predict the various phenotypic changes that occur when a given cancer and its cells are subjected to a drug and, better yet, based on the tool, propose various possible combinations of available drugs, as a rational combination strategy, to prevent the emergence of phenotypes that could drive further metastasis or recurrence.

Cancers of different tissues can nominally possess similar mutational signatures in their driver landscape, for example 38% of Breast Carcinoma, 19.2% of Colorectal Adenocarcinoma, and 10.6% of Endometrial Cancers contain PIK3CA mutations while 30.3% of Endometrial Cancer, 13.7% of Breast Carcinoma, and 12% of Colorectal Adenocarcinomas contain PTEN deletions and nulls [1]. In addition to having certain specific mutational signatures, cancers are often characterized by mutational heterogeneity and additional driver and passenger mutations that give the cancers a complex growth and metastatic advantage. While admittedly these cancers of different origins, having multiple different mutations, are often treated with specific inhibitors, the complexity imparted by the multiple driver mutations lend the cancer to be refractory to single therapeutic agent treatment. Emergence of resistance to single agent therapy can thus be overcome by employing combinations of drugs. While there are many drug combinations that have worked successfully for primary tumors and that have become resistant to single agent therapies or cancers with complex mutational backgrounds, problems abound as there is a severe paucity of rational, quantitative methods of design. Although estimates indicate that there are at least 50,000 plus clinical trials registered with the FDA, most combination drugs are heuristic, qualitative and are based on assumed additive effect. For example, using a combination of Palbociclib (CDK inhibitor) plus Afatinib (pan ERBB inhibitor) in esophageal carcinoma due to assumed synthetic lethality of synergistic activation or using Palbociclib (CDK inhibitor) plus anti-PDLI (check point therapy) in colorectal cancers due to expected synergistic effects.

The methodology proposed here is based on the idea of projecting the cancer cells onto a multidimensional phenotypic space achieved by mapping the high throughput 'omics, captured by way of single-cell RNA seq (scRNA-seq) or single-cell ATAC seq (scATAC-seq) of the cancer cells, to the corresponding phenotypes. Optimality and rationality of combination therapy would then be achieved by ensuring that the trajectory that the cells traverse in the multidimensional phenotypic space during therapy is away from phenotypes like stemness, mesenchymal like, survival or autophagy which could contribute to resistance to therapeutics and drugs. The major innovation here is that a single cell is mapped to a set of phenotypic values in a multidimensional phenotypic space by using Deep Learning/Machine Learning. Thus, cellular changes that occur during inhibitor therapy in cancer are visualized as trajectories in the phenotypic space. Furthermore, rational drug combinations are designed based on an optimal trajectory in the phenotypic space that would for example move all the cells to the death or apoptosis dimension. The research proposed is translational in nature as it can be easily deployed in clinics and cancer centers by simply performing scRNA-seq plus ATAC-seq on the tumor cells which, on applying to the neural network, will project the cells of the tumor into the multi-dimensional phenotypic space. Using a database of previously existing drugs and their effect on the cells in the space in terms of the trajectories, this project proposal aims to predict the rational combinatorial drug designs that will ensure optimal efficacy of the drugs.

The explosion of high throughput 'omics for the measurement of the internal states of the cells (deep sequencing, single cell RNA and ATAC sequencing, single mass spectrometry for protein sequencing) have opened up hitherto unexplored avenues for mapping the internal states of the cells to the external phenotypes that have been used to traditionally measure cellular properties. Accompanied by the advances in the development and implementation of deep learning neural networks, the mapping of the internal states or the genotype of the cell to the external states or the phenotype may be developed. By virtue of this mapping, an individual's tumor cells can be projected onto a multidimensional phenotypic space and optimize the combinational cancer therapeutics in this space such that resistance and recurrence are minimized.

Genotype to phenotype mapping continues to be an open problem, by virtue of the description of the internal states and the external states. The multidimensional phenotypic space provides, by virtue of additional clustering on the phenotypic space, a way to visualize multidimensional data, such as scRNA-seq data. Tumor cells and the effect of therapy on tumor cells are visualized as a cloud of cells moving along a trajectory by virtue of a deep learning neural network (DL-NN). By building a database of trajectories of the cells for the different available classes of drugs and therapeutics, a rational, intelligent way of designing cancer drug therapies for a given individuals tumor can be designed and proposed by moving the cells away from phenotypes that indicate resistance to therapy and recurrence.

To model a combination therapy, a single cell is mapped to a set of phenotypic values in a multidimensional phenotypic space. Thus, cellular changes that occur during inhibitor therapy in cancer are visualized as trajectories in the phenotypic space. Rational drug combinations are designed based on an optimal trajectory in the phenotypic space that would, for example, move all the cells to the death or apoptosis dimension. Embodiments of the present disclosure are translational in nature, as these embodiments can be easily deployed in clinics and cancer centers by simply performing scRNA-seq plus ATAC-seq on the tumor cells, which, on applying to the neural net will project the cells of the tumor in the multi-dimensional phenotypic space. Using a database of previously existing drugs and their effect on the cells in the space in terms of the trajectories, embodiments of the present disclosure provide combinatorial drug designs that ensure optimal efficacy of the drugs.

Characterizing the WBCs in blood for clinical purposes in cancers, infections and medical needs is referred to as immuno-phenotyping. A deep learning (DL) net to map the cellular genotype to the phenotype is disclosed herein. Single cell RNA-seq data combined with tagging multiple cell surface epitopes is used to train the DL net. A fully trained DL net then predicts the phenotype from just the single cell RNA-seq.

The following describes technology for a mapping between the RNA expression and functional readouts in the context of immunophenotyping of human WBCs. Immunophenotyping is an expensive diagnostic test employed to characterize WBCs in clinical and research settings. A T-cell immunophenotyping in the context of a leukemia can cost upwards of $500 for the end user with the cost progressively increasing for other additions to a total of more than $1K for a complete WBC count. Immunophenotyping typically involves designing an exhaustive antibody panel as a marker (for ex. CD3+, CD4+, CD8+ and CD56+ for T-cells) for the various WBCs in the blood and subsequently using the expensive instrumentation of a multi-color flow cytometer to analyze the cells. The cells are typically flagged as positive or negative based on subjective and heuristic threshold levels set as gates in the flow cytometer and is excessively dependent on the flow cytometer operator leading to increased material, operator and diagnostic cost.

Single cell RNA-seq continues to be the workhorse of the 'omics world with prices per sample dropping recently to around $1K. Single cell RNA-seq provides a snapshot of the internal state of the transcriptomics of every single cell. Since the transcriptomics of a cell combines with the cellular machinery to make proteins which then determine the functional readout of the cell, learning the putative mapping of the transcriptome to the functional phenotype will enable the characterization of the cell. This would then enable the achievement of immunophenotyping of all the WBCs from a standard single cell RNA-seq experiment.

Deep learning, driven by exciting developments in hardware, software and ease of implementation, has the ability to learn interconnections and patterns in high dimensional data. Although the scRNA-seq data is a high dimensional 30,000×1000 (gene products×cells) sparse data matrix, various deep learning nets like a CNN (convolution neural network) with multiple hidden layers can learn the interconnectivity in the high-dimension data and classify the cells to the correct phenotype. To train such a deep learning CNN with multiple hidden layers, a technology based on a technique called CITE-Seq called Total-Seq can be used. In the Total-seq protocol single cells are also tagged with antibodies for epitopes that define the cells with the WBCs such that both the scRNA-seq and antibody tags are read off so that simultaneous scRNA-seq and cell surface epitope information for the same cell is available. Once trained, this deep learning CNN called ImmunoPhenoNET, which may be cloud based, will take as input standard scRNA-seq of human PBMCs and characterize the phenotype of the WBCs. ImmunoPhenoNET will also have options for querying T-cell exhaustion, T-cell heterotypic phenotype changes in AML and other cancers and diseases. Immunophenotyping and/or Flow Cytometry is figured to be a market between $1.5 to $5 billion as a diagnostic and analysis tool.

Mapping the internal states of a cell or a "genotype" to the physiologic manifestation of its function or the "phenotype" has remained an elusive and attractive problem in equal measures. While the internal states in mRNA expression and ATAC-seq are being measured with unprecedented resolution on a single cell level, the phenotypes in biology are measured by traditional biological assays. An application area that could benefit the most with the development of the genotype to phenotype mapping is immunophenotyping. Human PBMCs (peripheral blood mononuclear cells) are WBCs that comprise of T, B, NK, Monocytes, Neutrophils, Eosinophils and can further be divided in T-helper, T-cytotoxic, T-regulatory, B-mature, B-Naive and so on. The distribution, relative frequencies, and number of these various PBMC compartment can be revelatory about the underlying diseased conditions. Hence, immunophenotyping, which characterizes the various fraction of the PBMCs are of immense value. Known technology requires a 24 or more antibody panel to reliably map all of these various cells along with the use of expensive multicolored flow cytometer with the presence of the operator. Positive or negative and/or the presence of a small population of specialized cells are subjective calls made by the flow cytometer operator based on gates or thresholds that are set. These are also accompanied by high cost of diagnostic tests. Deep learning can capture the underlying patterns in multidimensional 'omics data on several levels of abstraction, for example, the interaction of the RNA expression leading to different protein level interactions which in-turn lead to different phenotypic outcomes can best be captured by a deep learning neural net. Thus, ImmunoPhenoNET addresses following aims:

Aim 1: To map the genotype to the phenotype a Convolution Neural Net (CNN) based deep learning net is built to mimic the propagation of information and interconnection that define the phenotypes of human PBMCs. As proof of principle, used publicly available databases from 10× Genomics where simultaneous reading of 13 cell surface epitopes and 30,000 genes from RNA-sequencing in human PBMCs are available as multiple experiments in different chemistries. The dataset may be divided into 90% training and 10% testing and implement a CNN with the 30,000 genes applied to the input layer, multiple hidden layers, and the 13 cell surface epitope readings as the output.

Aim 2: To build a database for the training of the human PBMCs genotype to the phenotype we use a modification of the CITE-Seq technique and develop an exhaustive database where the single cell RNA-seq values and cell surface markers corresponding to the immunophenotyping will be built. Using commercially available protocols like that of Total-Seq from Biolegend, the model may be diversified to include samples from ethnically different individuals and sex. This is then used to further train the CNN to improve the mapping.

In some embodiments of the present disclosure, a DL-NN explores the mapping between the cellular genotype (single cell RNA-seq plus ATAC-seq) and the measurable phenotype (apoptosis, survival, migration, autophagy etc., as measured by traditional biological assays) in mammalian systems and to investigate the suitability of the deep learning net to propose and achieve novel drug combinations in cancer therapeutics. Deep-learning architecture may be used to project tumor samples, by virtue of their single cell-RNA seq plus ATAC-seq measurement, into the multi-dimensional phenotypic space and query the position of cells altered in cancer and cancer therapeutics. Different drug combinations, specific to the position of the tumor cells in the multi-dimensional phenotypic space, can then be designed as trajectories in this space leading the cells to areas of more killing and less survival. The multidimensional phenotypic space is set up by using a convolutional neural network (CNN) based architecture to learn the mapping between the scRNA-seq/scATAC-seq data and the cell surface markers in chosen representative cancer cell lines. This can be achieved by using a modified CITE-seq protocol, where single cells can be analyzed by either scRNA-seq or scATAC-seq and tagged with labels to measure up to 150 plus cell surface markers. Thus, embodiments of the present disclosure offer a way to map the genotype to the phenotype and provides an alternate way to visualize scRNA-seq data, while also providing a rational, intelligent way to design combinatorial drug therapy for personalized cancer treatment.

Embodiments of the present disclosure consider and evaluate alternative DL-NN architectures and propose novel ones for addressing the task of exploring the interconnections between the multidimensional-omics, from single cell genotype measuring techniques like single cell RNA-seq (scRNA-seq) and ATAC-seq, and the phenotype data measured from biological assays. Traditional biological assays, provide means to measure quantitatively various fundamental phenotypes like cellular survival, apoptosis, migration and stemness to name a few, often in ratios, percentages and arbitrary units. Additionally, advances in single cell genomic techniques like scRNA-seq for transcriptomics, single cell ATAC-seq for epigenomics to harness the inherent cell to cell variability have introduced the notion of a family of responses to external stimuli in a group of cells. The grand challenge then is to integrate single cell measurements of the genotype and map the genotype to the phenotype. Consistent with the analysis of thousands of single cells and the generation of large amounts of 'omics data is the need for accurate representation and visualization of multidimensional data. While current methods rely on heuristically curated gene sets and lists (Gene Ontology and Gene Set Enrichment Analysis), these methods are oblivious to either a positive or a negative contribution from a particular gene or the various interconnection between them. The DL-NN architecture-based mapping captures both the genotype to phenotype map and the nature of the interconnections between the genes that contribute to a given phenotype by virtue of the structure of the neural network including the weights of the interconnection between the nodes.

Quantitative Mapping of the Internal States to Phenotypic Measurements and Structuring the Phenotypic Space Embodiments of the present disclosure include a multilayer artificial neural network (ANN) with 'omics data applied to an input, many interconnected hidden layers, and an output layer corresponding to the phenotypic measurements data. Learning of this mapping can be achieved during the supervised training of the neural network wherein the parameters of the network are estimated.

Representation of Cancer Cell and Therapies in Phenotypic Space

A tumor is composed of a heterogeneous group of cells with distinct properties. Each of these cells has a unique signature in gene and protein products and by virtue of the mapping to the phenotypic measurement, each signature can be represented by projections onto the different phenotypic axes.

Rational Combination Drug Design as a Drug Therapy

This can be thought of as a multidimensional optimization problem in the phenotypic space. A database of selected drugs and combinations that cause known phenotype effects for a given cancer is built, and then a selection is made of an optimal combination of those drugs.

Intelligent Design of Cellular Perturbations Based on a Multidimensional Phenotypic Space The genotype refers to the internal states of the cell, i.e., the genotype (genes), the epigenetic landscape, the gene expression (mRNA) patterns that arise out of the combination of the genotype and the epigenetic regulation and the myriad proteins that are produced from the mRNA and the various post-translational modifications that are imparted to the proteins. The phenotype refers to the external manifestation of the cellular response and properties and is defined as a measurable trait like proliferation, migration, stemness, mesenchymal like and so on. The interesting aspect of phenotypes beyond the utility as a measure of cellular properties is the fact that traditional biology in recent decades has dealt with in terms of phenotypes. For example, when cancer cells are treated with inhibitors, the readout for the efficacy of the drugs is in terms of phenotypes like proliferation, cell-division and emergence of properties like autophagy, migration and stemness etc.

Decades of study and analysis have also produced many different assays for the measurement of these properties like the MTT assay for proliferation and the identity of many cell surface markers as surrogates for cellular phenotypes like CD45 for cells of immunogenic nature. The behavior of a cell to an external stimulus or signal can also be understood and characterized succinctly in terms of the genotype and the phenotype-when an external stimulus binds to and signals inside a cell, a network of signals come together to transduce and communicate the signal down to the genotype. In response to a signal, a cell can alter its epigenetic landscape, thus changing the gene expression patterns (mRNA) of all the affected genes, then altering the corresponding proteins produced from the respective mRNA—this then could lead to an altered phenotype of a cell (FIG. 1), for example, in response to a chemokine the cell could start migrating in the direction of the arrival or gradient of the chemokine. Thus, in response to a signal the internal state of a cell can change resulting in a corresponding change in its external state or the phenotype.

The behavior of a living cell is a complex function of both its internal states and the extracellular environment. The internal states, as defined by the genetically determined biochemical networks, dictate the inter-dependence of activities of various molecules and molecular circuits controlling diverse cellular phenotypes. Even in isogenic populations, the variability in the levels and activity of the nodes in these networks result in concomitant variability in the phenotypic response producing a family of responses to a given external stimulus in individual cells. The dual limitation of fragmented analysis of biological systems and the relative novelty of characterization of cell variability, has hindered the development of an integrated view of cell behavior defined as a function of internal states, external inputs, and phenotypic outcomes to biochemical treatments. The challenge is to discover this mapping between the multi-dimensional internal states of the cellular processes and the corresponding multi-dimensional phenotypes, and to harness this information to design intelligent perturbations of cell behavior in research and clinical settings (as shown in FIG. 1). This mapping is a systems paradigm for designing intelligent network perturbations, and ultimately new clinical interventions.

system method of mapping internal states onto measurable phenotypes, as an alternative to pre-curated lists. Table 1 illustrates representative phenotypes used for enumerating axes for phenotypic space and cell lines used to measure phenotypic values.

TABLE 1

| Cell Lines | Ki-67 % | Annexin-V (%) | Migration (um/hr) | Cell-cycle arrest % | AutophagyLC3B stain | OxPhos % | Survival % cells |
|---|---|---|---|---|---|---|---|
| MCF10A | 23 | 2 | 0.01 | 45 | 0.5 | 35 | 85 |
| MB-231 | 75 | 15 | 25 | 2 | 15 | 45 | 90 |
| BT474-1 | 0.1 | 55 | 25 | 90 | 90 | 50 | 15 |
| SKRr3-2 | 95 | 5 | 0.5 | 25 | 33 | 15 | 75 |

FIG. 1 is an integrated view of cell behavior and mapping of internal states to phenotypes. As shown in model 100, external inputs 101 may be associated with one or more internal states 102. External inputs 101 and the associated internal states 102 may then be organized as a series $a_1$ through $a_n$. Once input, the mapping 103 of the series $a_1$ through $a_n$ to the series $b_1$ through bn occurs, resulting in output phenotypes 104 for each external input. Phenotypes 104 may include migration, survival, or apoptosis.

Multidimensional Phenotypic Space as a Representation of Cellular Homeostasis and its Perturbations Cellular homeostasis and its perturbations can be represented not only in terms of their genetic, epigenetic, and proteomic signatures but also as a group of distinct, measurable phenotypes referred to here as the phenotypic space. This is advantageous as biological function is ultimately expressed in phenotypes-functional changes, such as a) emergence of cancer from normal cells, b) developmental processes, e.g., renewal and differentiation of stem cells, c) wound healing, d) evolution of tumor under drug treatment, e) emergence of aggressive migratory cancer cells, reflect the underlying phenotypic plasticity (FIG. 1). On a single cell level, there is also a benefit from relating genetic and proteomic cell states to measurable and quantifiable phenotypes, e.g., cell division, migration, death (apoptosis), differentiation, metabolic state, to name a few. Unfortunately, these phenotypes are frequently studied in isolation, leading to unanticipated effects including side effects in cancer treatment. The key is to characterize and populate a multidimensional phenotypic space, in which a cell is simultaneously characterized not by a single but by multiple phenotypic values, akin to coordinates within a space. The goal is to characterize how these phenotypic coordinates for a given cell are defined by the internal cell states.

The advent of the recent ’omics explosion has resulted in multiple new ways to measure the internal states of a cell by single cell RNA-seq, single cell epigenomics or Mass-Spectrometry based large scale analysis. The discrete, digital nature of the ’omics measurements-differential expression in gene products or peptides and the multidimensional size (Number of cells~100s×number of genes~10,000s) make for a relatively straightforward quantitative representation while the notion of a phenotypic measurement is still very generic. It is tempting to infer phenotypic states from genomic and proteomic datasets by using pre-curated lists (Gene-Ontology) that don’t accurately capture the mapping of the descriptive cell behavior (phenotypes) to the underlying genotypes. The embodiments disclosed herein illustrate a Quantitative Mapping of the Internal States to Phenotypic Measurements and Structuring the Phenotypic Space:

The mapping of the massive single-cell ’omics sequencing data (corresponding to the internal states) to the relatively sparse phenotypic measurements falls squarely within the ambit of deep learning/artificial intelligence/neural networks. Embodiments of the present disclosure include a multilayer artificial neural network (ANN) with the ’omics data applied to the input, two to three interconnected hidden layers and the output layer corresponding to the phenotypic measurements data. Learning of this mapping can be achieved during the supervised training of the neural network wherein the parameters of the network are estimated. For the example in Table 1, there are seven phenotypic measurements corresponding to cell division (Ki-67 staining), apoptosis (Annexin-V staining), Migration (in microns/hour), cell-cycle arrest (Comet assay as %), autophagy (LC3B staining percentage), OXPHOS state (Mito-tox stain) and Survival (Cell-titer glo assay). Using four cell lines MCF10A (normal breast epithelium), MDA-MB-231 (triple negative aggressive breast cancer cell line), BT474-1 (Her2+ breast cancer cell line treated with Her2 inhibitor) and SKBR3-2 (Her2+ breast cancer cell line stimulated with Epidermal Growth Factor (EGF), Table 1 may be populated by running the various listed assays. A single cell RNA-seq on 100 cells for each of these four cell lines would give a {Number of genes×100} dataset for each cell line. For MCF10A for example, this dataset {No. of genes×no. of cells} is applied to the input of the neural network and the output of the network is set as the first row in Table 1 corresponding to MCF10A. The training algorithm now varies the neural network parameters until the network output matches the row of Table 1. This is repeated for all the cell lines in sequence until the neural network captures the mapping. Ideally the above example would at least include as many cell lines as the number of phenotypes such that every phenotype is represented or enumerated. Given the recent advances in cloud computing and deep learning hardware, the neural net is proposed to be implemented on a highspeed cluster or multiple NVIDIA Turing cards and the training is expected to take a few days if not hours. This analysis results in predictive modeling of how multidimensional phenotypic inputs are defined by multidimensional internal states.

Representation of Cancer Cells and Therapies in Phenotypic Space

Figure 2:
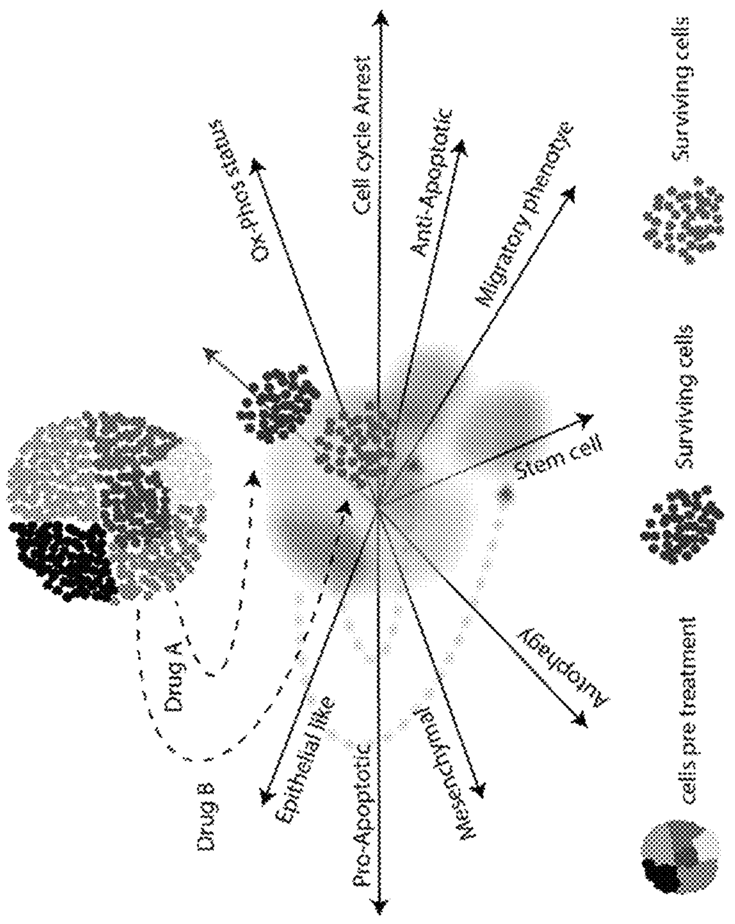
FIG. 2 is a representation of tumor cells and trajectories of drug treatment in the phenotypic space, in accordance with one or more embodiments of this disclosure.

FIG. 2 is a representative of tumor cells and trajectories of drug treatment in the phenotypic space. A tumor is often composed of a heterogenous group of cells as shown in FIG. 2 where the different colors represent cells with distinct properties. Each of these cells has a unique signature in gene and protein products and by virtue of the mapping, can be represented by projections onto the different phenotypic axes. Simply put, if the BT474 Her2+ breast cancer cells were to be analyzed via single cell RNA-seq and applied as input to the previously trained deep learning neural-net, it would yield output values corresponding to the seven different phenotypic measurements. This can be interpreted as points and a group of cells as a cloud in the phenotypic space (FIG. 2). When the BT474 cells are treated with an inhibitor (drug A in FIG. 2), the cells undergo considerable changes in their internal states, which result in a change in their position in the multi-dimensional phenotypic space, for example moving towards the apoptotic axis and then the surviving cells are expected to rewire their internal states and end up at a different unique point tracing a trajectory in phenotypic space as shown in FIG. 2. Expectedly, treatment with a different drug (drug B) can produce a different trajectory of survival for the cells. This analysis can test the developed model and train it further.

Intelligent Perturbation as an Innovative Drug Therapy

Cancer has remained a stubbornly resilient malady to cure. Targeted cancer therapies in the clinics are unidimensional in their objectives because the drugs are designed to inhibit the function of the mutated/overexpressed protein. Cancer cells can develop multiple mechanisms to circumvent single point pathway inhibition. This leads to considerable rewiring in the surviving cells which acquire new properties to devastating effects. The surviving cells can remain dormant, switch phenotypes, or develop new mutations to become drug resistant. Based on the idea of the multidimensional phenotypic space and the tracing of trajectories in the phenotypic space, an intelligent perturbation for cancer therapeutics is an optimal trajectory through this space such that the surviving cells are smaller in number and do not acquire important new properties. This can be thought of as a multidimensional optimization problem in the phenotypic space and the solution to this optimization problem is the intelligent perturbation. Embodiments of the present disclosure address this by building a database of selected perturbations that cause known phenotype effects for a given cancer and then select an optimal combination of those perturbations over all of the possible combinations.

Figure 3:
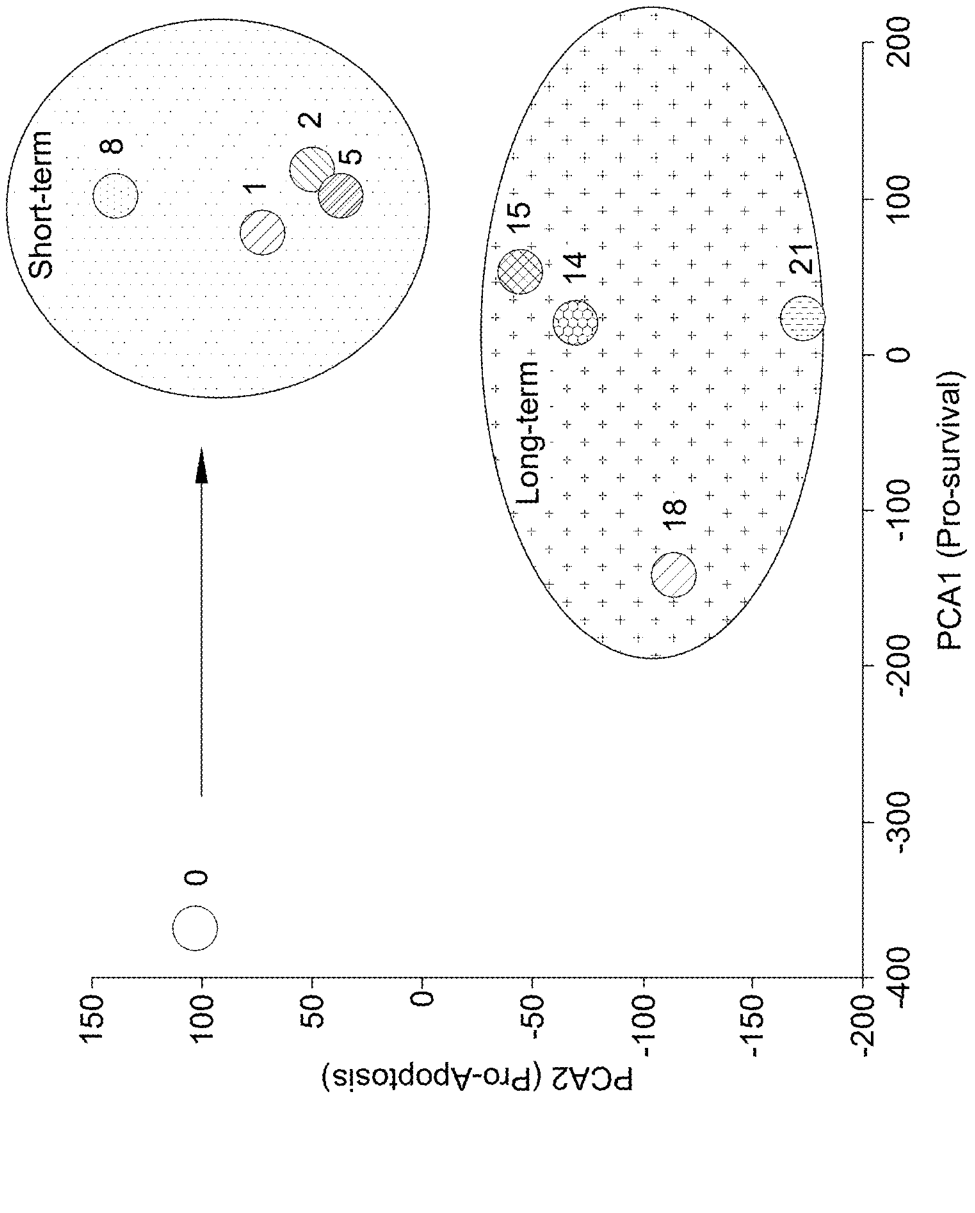
FIG. 3 is a schematic illustrating an optimal trajectory through phenotypic space as a combinational drug therapy, in accordance with one or more embodiments of this disclosure.
Figure 5:
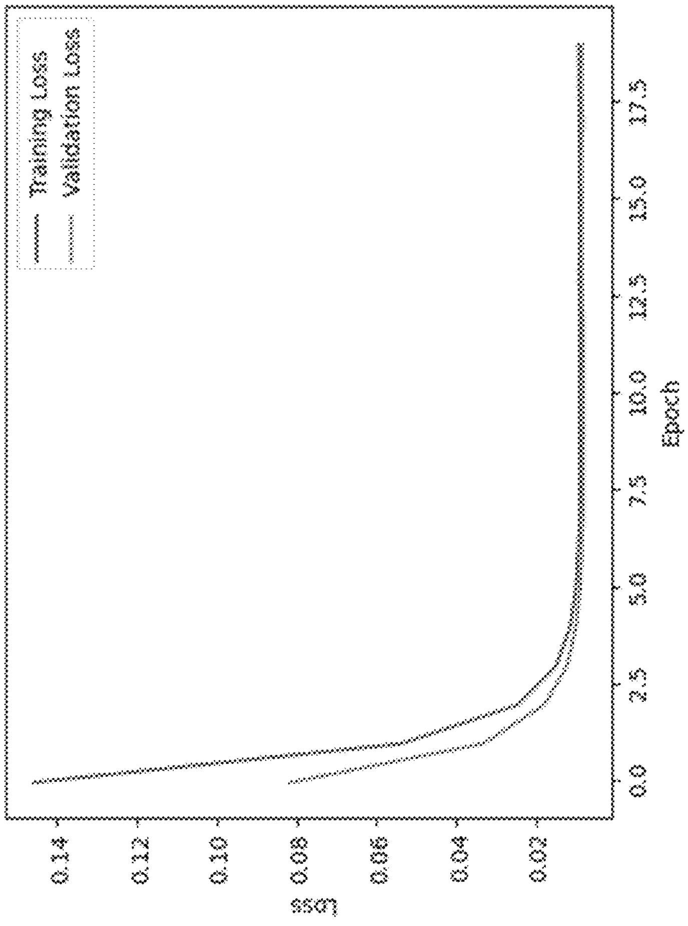
FIG. 5 is a graph of a validation model for the feedforward neural network, in accordance with one or more embodiments of this disclosure.
Figure 6A:
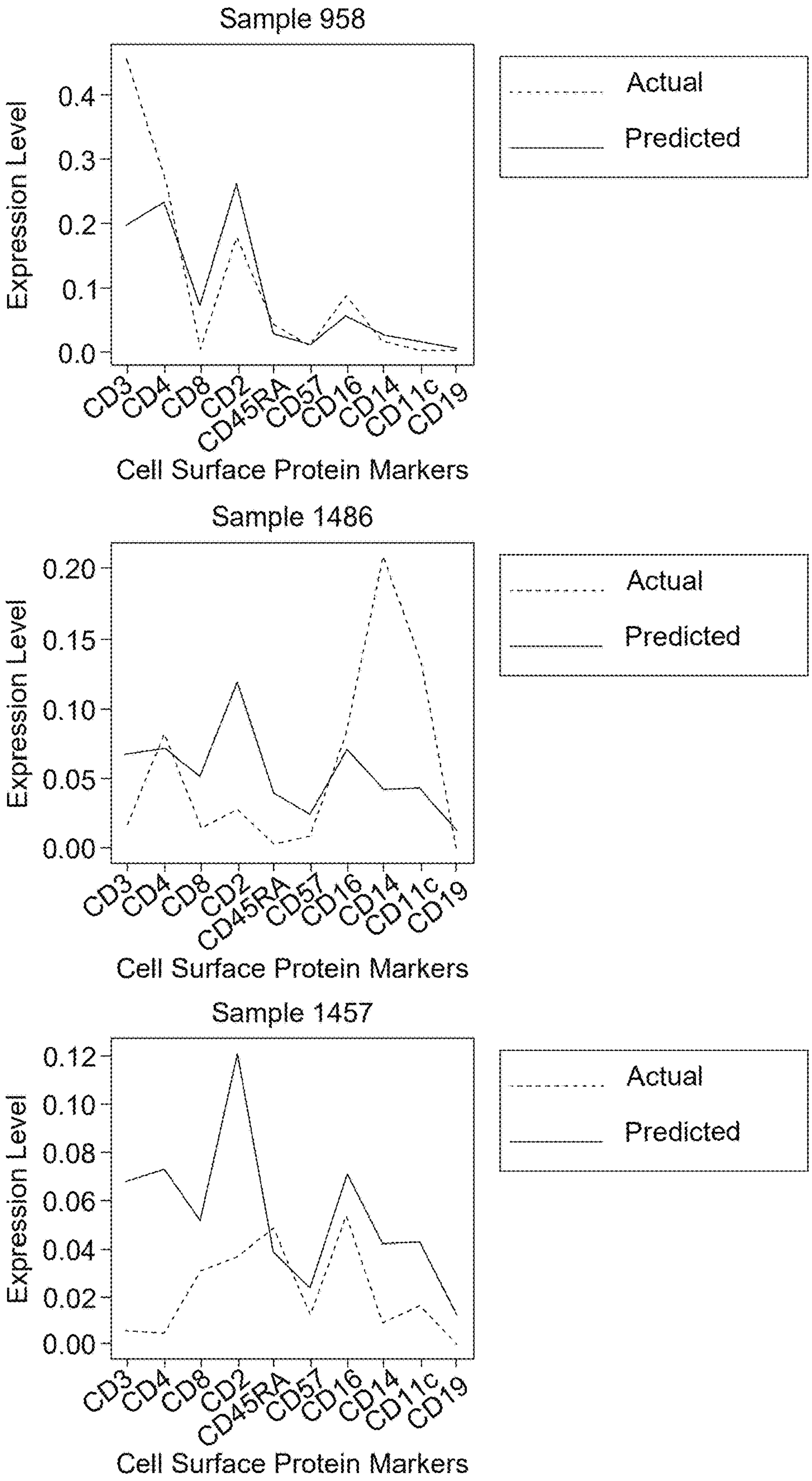
FIG. 6 is a series of validation graphs for a variety of sample cells, in accordance with one or more embodiments of this disclosure.
Figure 6B:
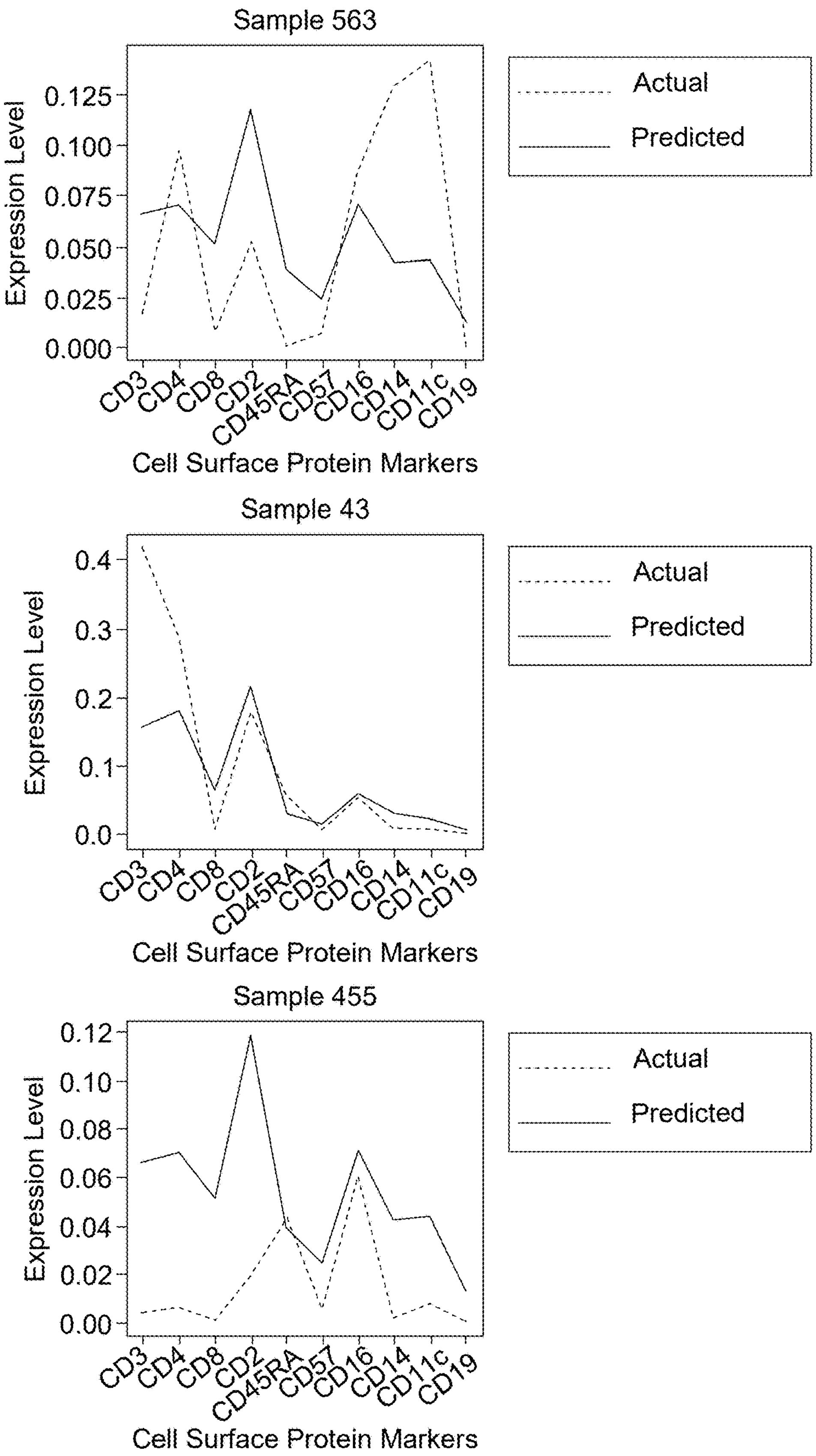
Figure 6C:
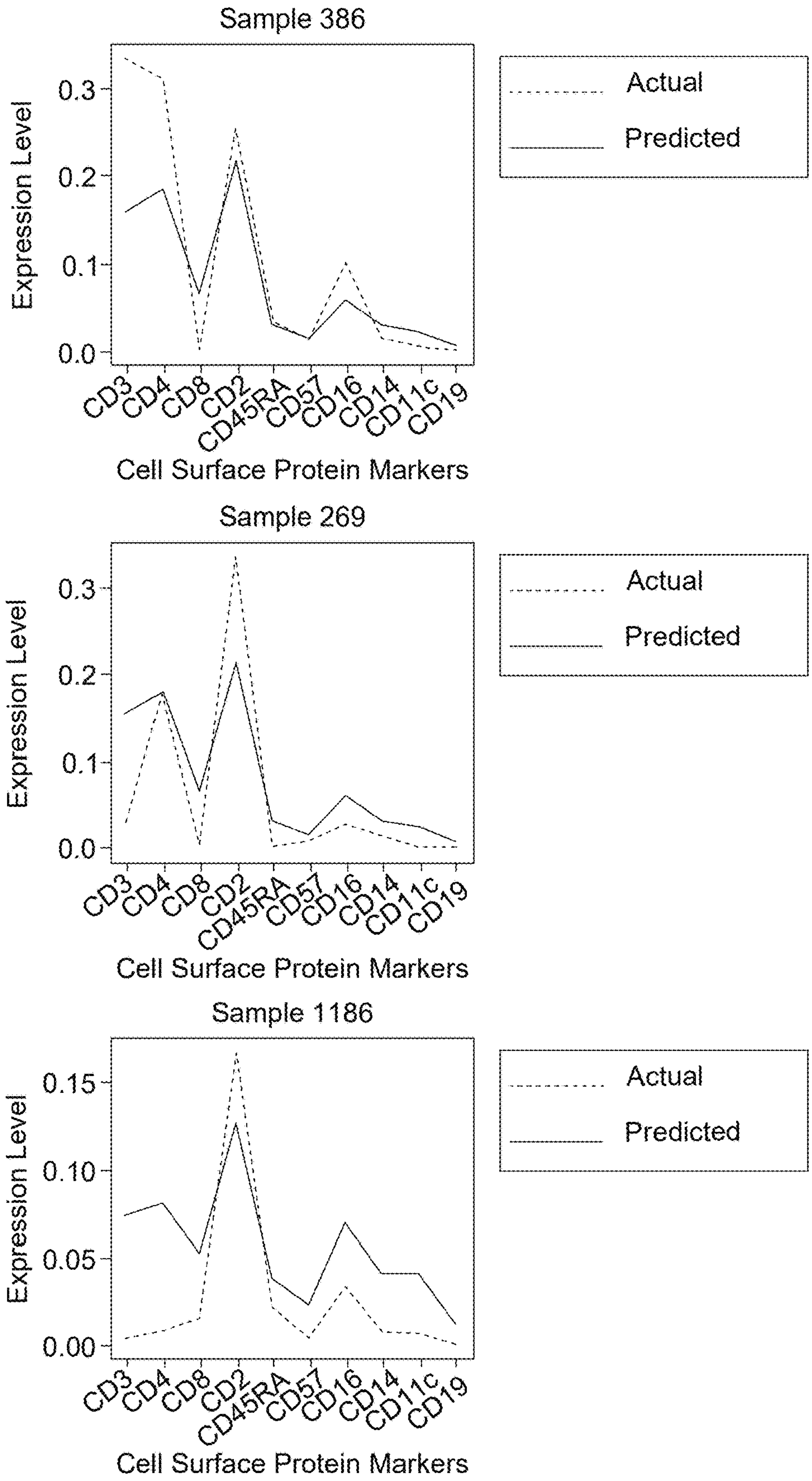
Figure 6D:
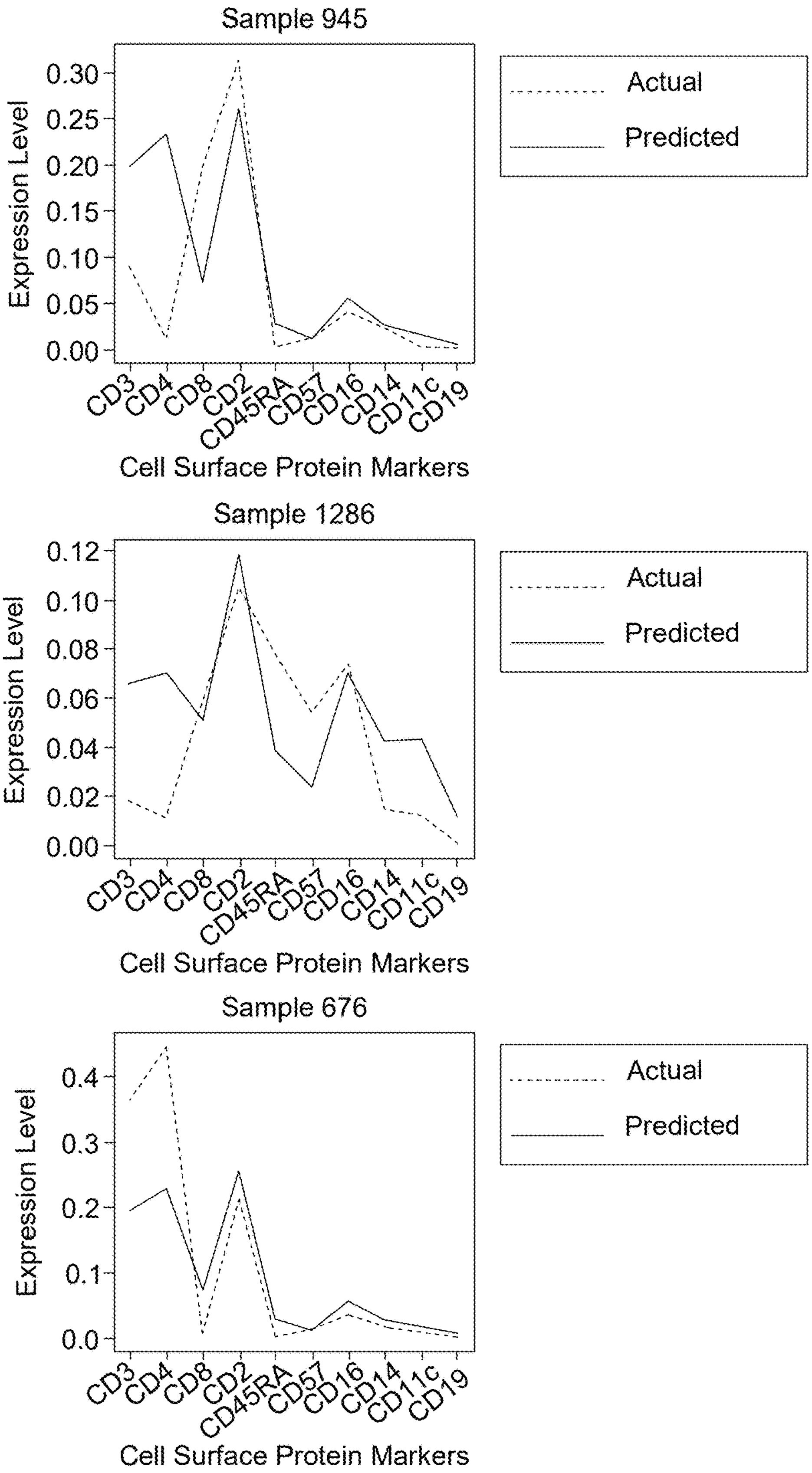
Figure 6E:
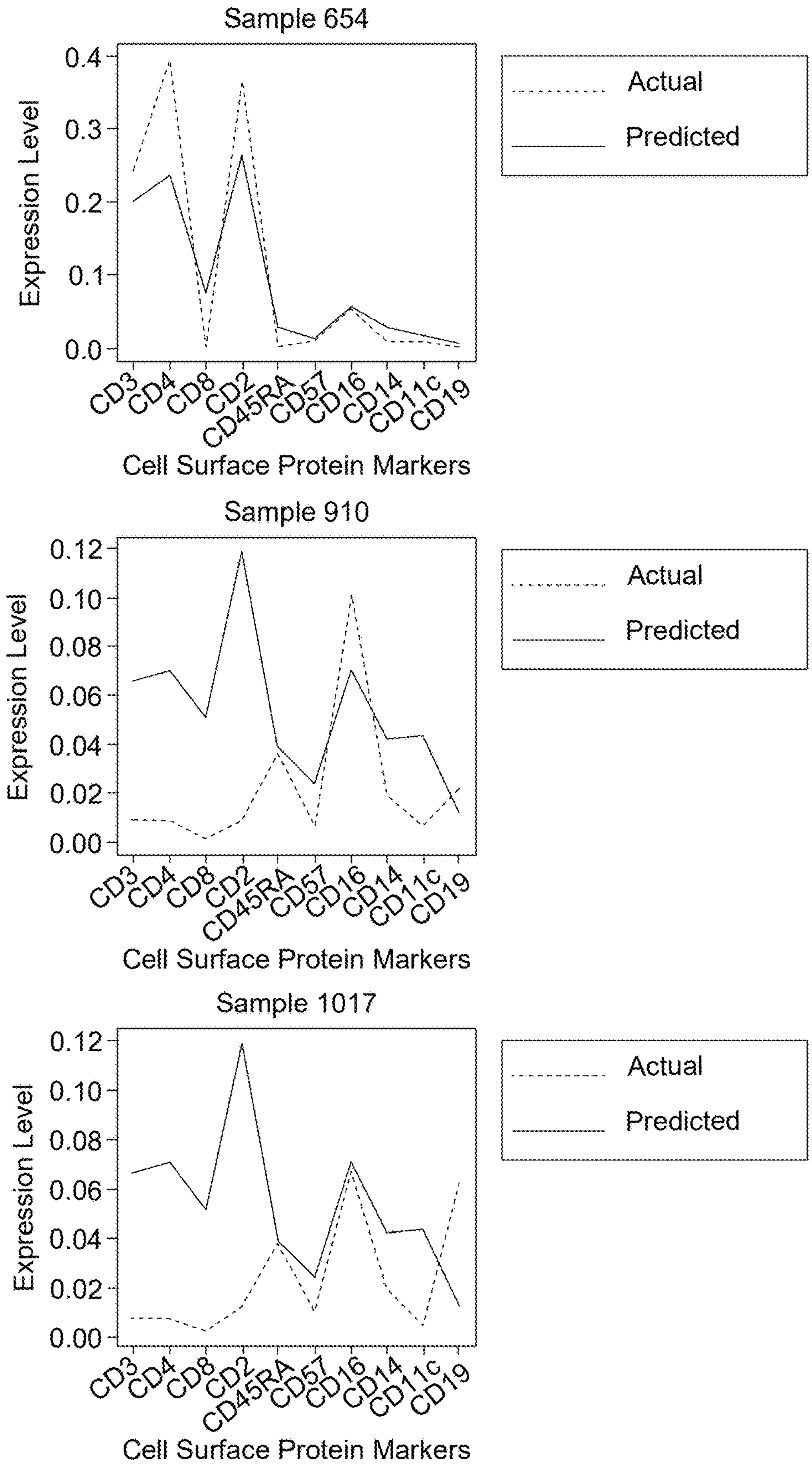

The comparison of the final and initial states of the cells treated with inhibitors allows the use of intelligent drug design as the new state can reveal existing vulnerabilities that can be exploited. As preliminary data, BT474 cells are treated with PI3K inhibitors for the indicated days until 21 days as shown in FIG. 3, analyzed by bulk RNA-seq followed by PCA based on GO ontology of apoptosis. The treated BT474 cells develop pro-survival properties over long-term treatment (FIG. 3) along with altered cell-cycling and ox-phos status. This approach can also bring exceptional power to bear on combination and sequential therapies. FIG. 3 illustrates an optimal trajectory through a phenotypic space as a combinational drug therapy.

Feedforward Neural Network Architecture

In some embodiments, an improvised feedforward neural network architecture may be used to map the input cell 'omics to the phenotypic measurements. An exemplary feedforward neural network is shown in FIG. 4. The feedforward neural network architecture may comprise an input layer, a first hidden layer, a first dropout layer, a second hidden layer, a second dropout layer, and an output layer. As shown in FIG. 4, the feedforward neural network 400 comprises an input layer 401 with 17014 features. The first hidden layer 402 may include 64 neurons, a ReLU activation function, and a L2 Regularization with lambda equal to 0.001. The dropout layer 403 may have a dropout rate of 0.5. A second hidden layer 404 may include 32 neurons, a second ReLU activation function, and a second L2 Regularization with lambda equal to 0.001. The second dropout layer 405 also has a dropout rate of 0.5. The final output layer 406 includes 10 neurons, as well as a linear activation regression. Example code for the neural network 400 is shown below:

```
from tensorflow.keras import reqularizers
from tensorflow.keras.models import Sequential
from tensorflow.keras.layers import Dense, Dropout
from tensorflow.keras.callbacks import EarlyStopping
# Buildinq the model
feedforward_mode13=Sequential ()
feedforward_mode13.add(Dense(64, activation='relu',
kernel_regularizer=regularizers.12(0.001), inuput_shape=
(X_train.shape[1].)))
feedforward_mode13.add(Dropout(0.5) ) # Increase dropout
rate
feedforward_mode13.add((Dense(32, activation='relu',
kernel_regularizer=regularizers.12(0.001)))
feedforward_mode13.add(Dropout(0.5)) # Increase dropout
rate
feedforward_mode13.add(Dense(10, activation='linear')) #
Linear activation for regression
# Compilinq the model .
feedforward_mode13.compile(optimizer='adam',
loss='mean_squared_error')
# Define early stoppinq callback
early stopping=EarlyStopping(monitor='val_loss',
patience=10,
restore_best_weiqhts=True)
# Traininq the model with early stopping
History3=feedforward_mode13.fit(X_train, y_train,
epochs=50, batch size32, Validation split=0.1, callbacks=
[early stopping])
```

Adding dropout layers randomly sets a fraction of input units to zero during training, reducing overfitting by preventing units from co-adapting too much. Reducing the number of neurons simplifies the model, decreasing its capacity to learn complex patterns and thus reducing the risk of overfitting. Early stopping halts training when the validation loss stops decreasing, preventing overfitting by finding the optimal point of generalization. L2 regularization with lambda 0.001 in the dropout layers adds a penalty term to the loss function, discouraging large weights and promoting simpler models, further preventing overfitting.

Reducing the dimensionality of the gene expression data from 17014 to 3158, as shown in FIG. 4 in the input layer and the first hidden layer, uses principal component analysis (PCA) to allow for more efficient processing and analysis while preserving most of the data's variance. This leads to more interpretable models and insights, as well as improved generalization performance due to a reduced risk of overfitting. Additionally, the compressed representation facilitates visualization and exploration of underlying biological patterns, aiding in the identification of relevant features and enhancing the robustness of research findings.

Using the Reduced PCA Data in the Neural Network

In some embodiments, an improvised feedforward neural network architecture may be used to map the input cell 'omics to the phenotypic measurements. An exemplary feedforward neural network is shown in FIG. 4. The feedforward neural network architecture may comprise an input layer, a first hidden layer, a first dropout layer, a second hidden layer, a second dropout layer, and an output layer. As shown in FIG. 4, the feedforward neural network 400 comprises an input layer 401 with 17014 features. The first hidden layer 402 may include 64 neurons, a ReLU activation function, and a L2 Regularization with lambda equal to 0.001. The dropout layer 403 may have a dropout rate of 0.5. A second hidden layer 404 may include 32 neurons, a second ReLU activation function, and a second L2 Regularization with lambda equal to 0.001. The second dropout layer 405 also has a dropout rate of 0.5. The final output layer 406 includes 10 neurons, as well as a linear activation regression. Example code for the neural network 400 is shown below:

```
# Evauating the model
pca_loss =feedforward_model4.evaluate(X_test_pca, y_test)
print("Test_Loss:", pca_loss)
50/50 [==============================]-0s 3ms/step-loss: 00086
Test Loss: 0.008555447682738304
from scipy.stats import pearsonr
y_test_pca=y_test.values.reshape(-1)
y_pred_pca=y_pred_pca.reshape(-1)
correlation coefficient, p_value: pearsonr(y_test_pca, y_pred_pca)
print ("Correlation Coefficient:", correlation_coefficient)
print("P-value"|p_value),
Correlation Coefficient: 0.6573292201514205
P-value: 0.0
```

Data Preparation and Preprocessing

Figure 7:
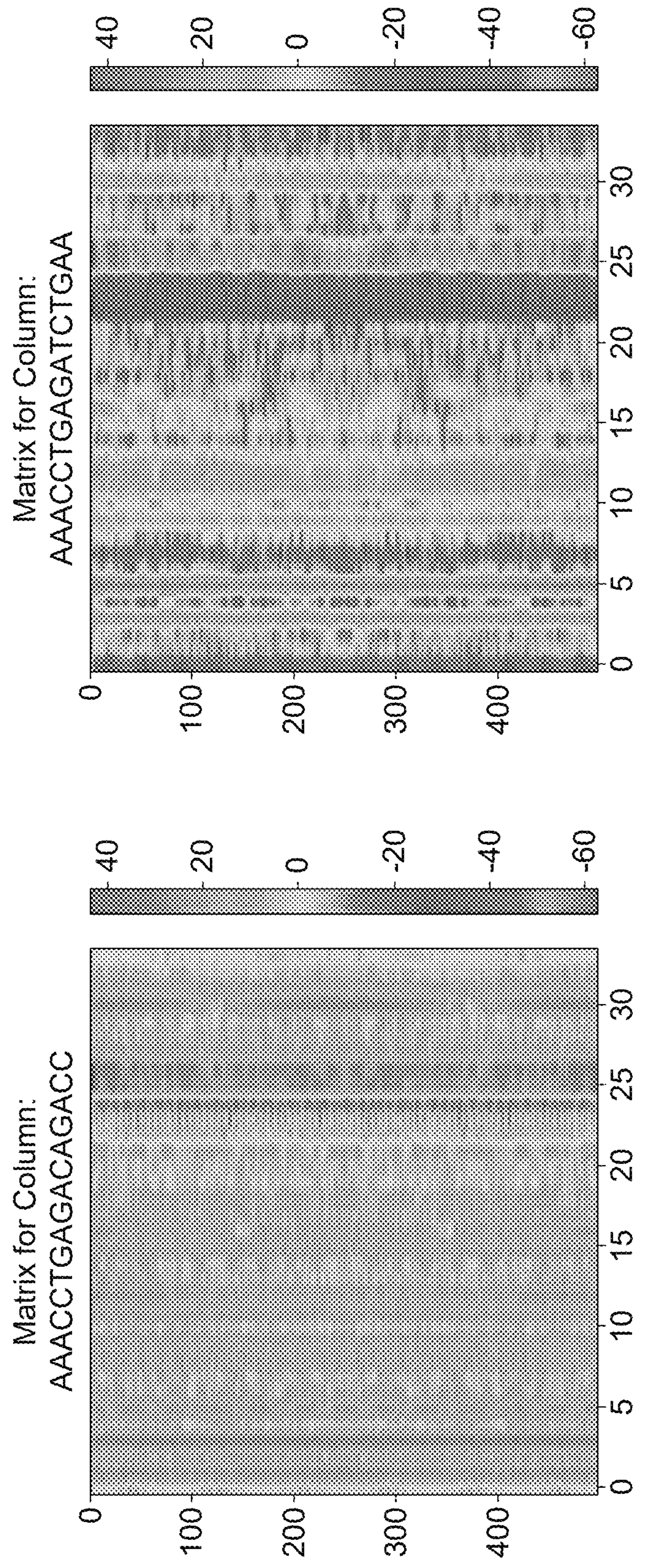
FIG. 7 is a series of exemplary image pools, in accordance with one or more embodiments of the present disclosure.

In some embodiments, a windowing technique is used within the feedforward neural network to break down the large, complex data input into manageable segments for analysis. A window length of 500 for each cell may be used for all protein samples. A short-time Fourier transform (STFT) may be used to transform protein expression data from each window into the frequency domain, thereby enabling the analysis of periodic patterns crucial for understanding cellular function in genomics. The frequency domain analysis can enhance pattern recognition and noise reduction, revealing critical biological signals and improving data quality for machine learning models. Frequency analysis may be visualized as a spectrographic image. These images can be produced by encoding the frequency spectrum over time into images, aiding in the interpretation of cellular processes and protein dynamics. Exemplary spectrographic images are shown in FIG. 7.

Figure 8:
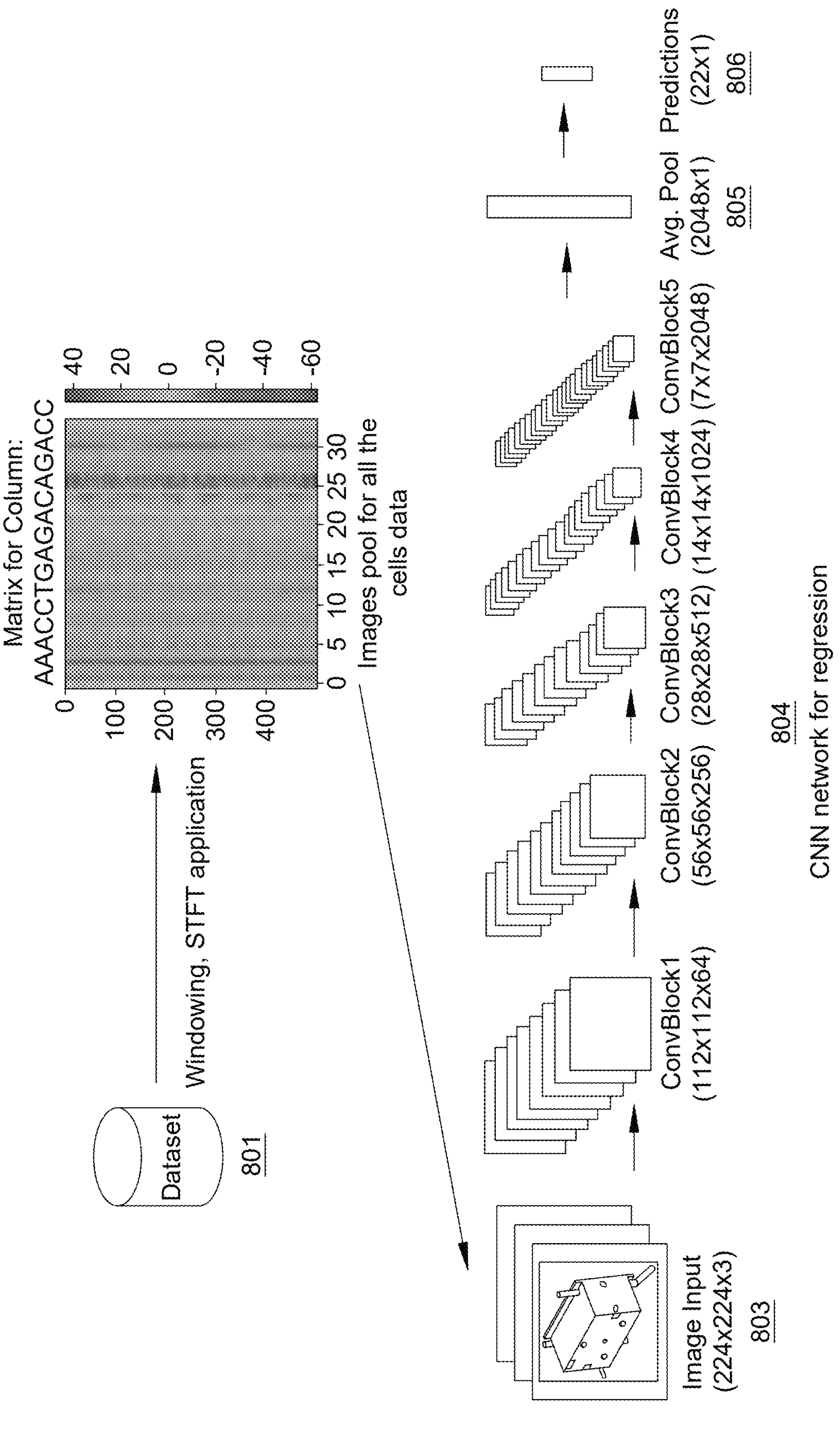
FIG. 8 is an exemplary process diagram of a convolutional neural network using a regression function, in accordance with one or more embodiments of the present disclosure.

FIG. 8 is an exemplary process diagram 800 of a convolutional neural network using a regression function. A dataset 801 is input to a preprocessing stage, where windowing and STFT functions are applied. An image pool 802 is created, for all cell data. An image input 803 is formed from the image pool 802. The image input 803 may have a dimension of 224×224×3. The image input 803 is provided to a convolutional neural network (CNN) for regression 804. The CNN may have five blocks of decreasing dimensional measurements. The CNN output may include an average pool 805, which is used to determine the predictions 806.

Figure 9A:
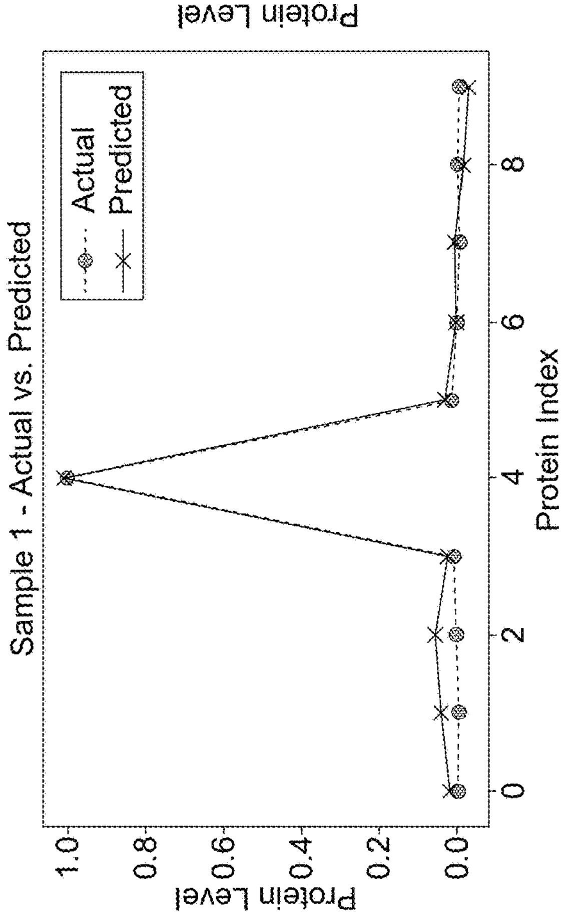
FIGS. 9A-9C are graph results combining the best features of the feedforward neural network, in accordance with one or more embodiments of the present disclosure.
Figure 9B:
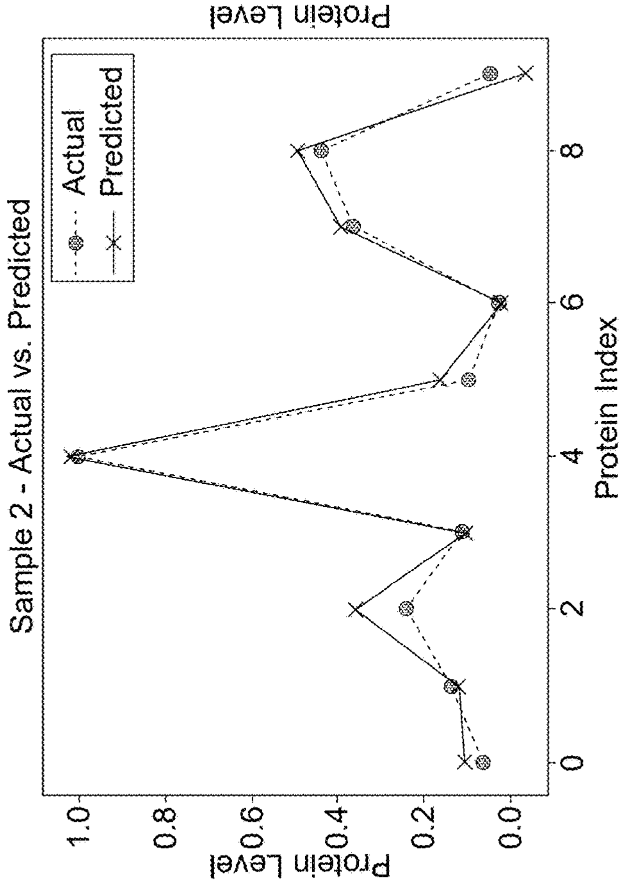
Figure 9C:
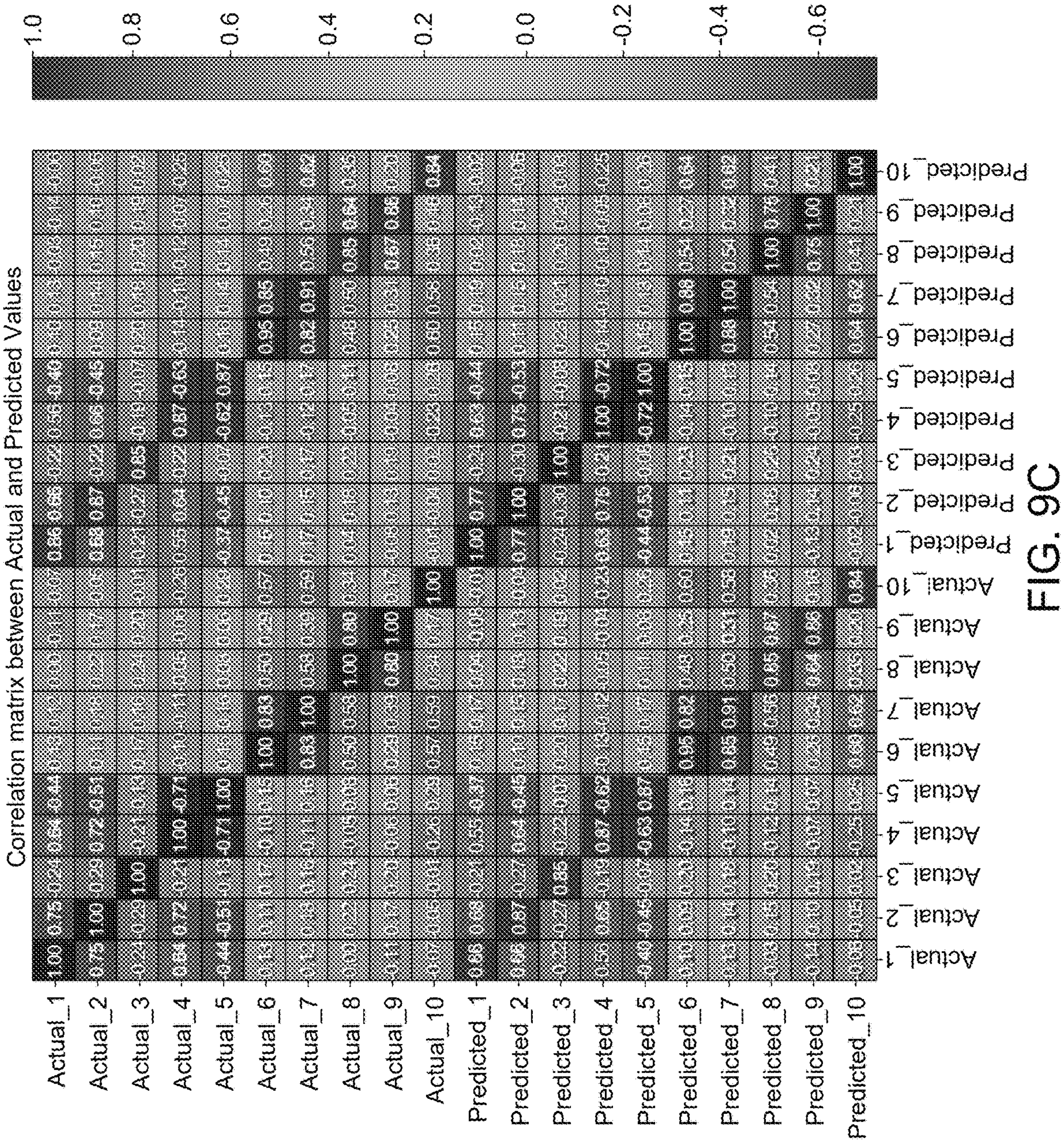

FIGS. 9A-C are exemplary graphs (FIG. 9A-B) of the results after combining the best features of resnet 50 and vgg16 together and using them as one model for best performance. A correlation matrix between actual and predicted values is shown in FIG. 9C.

Results for Deep Learning Network

Figure 10:
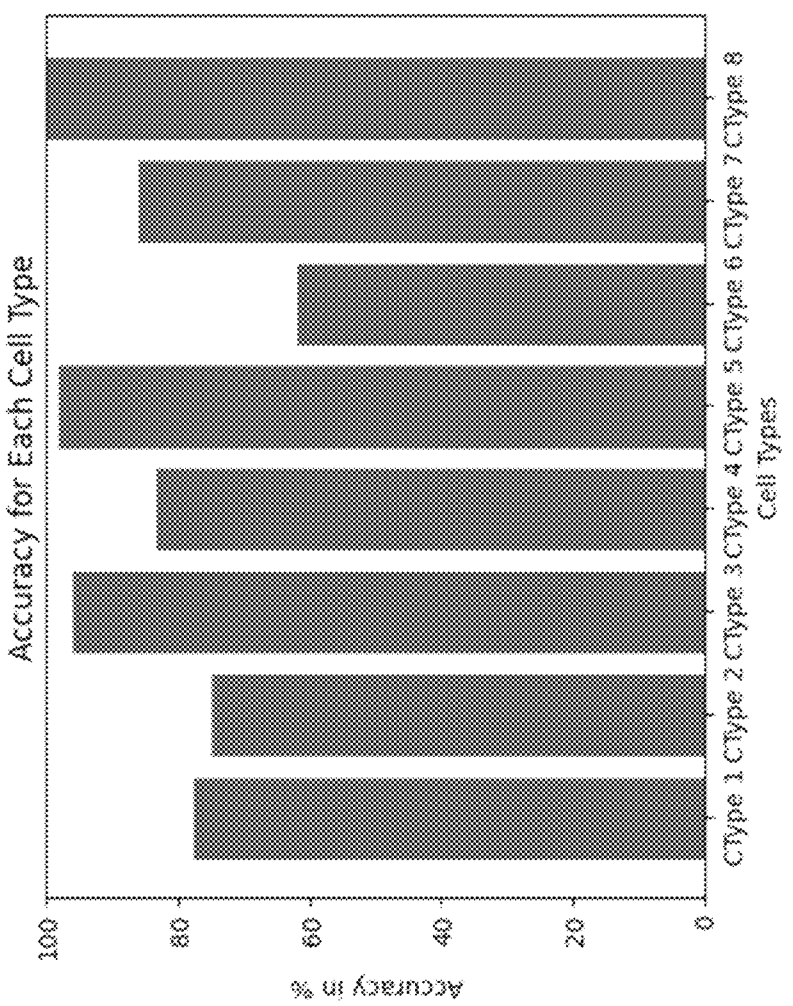
FIG. 10 is a graph illustrating the prediction accuracy of PBMC clusters, in accordance with one or more embodiments of the present disclosure.
Figure 11:
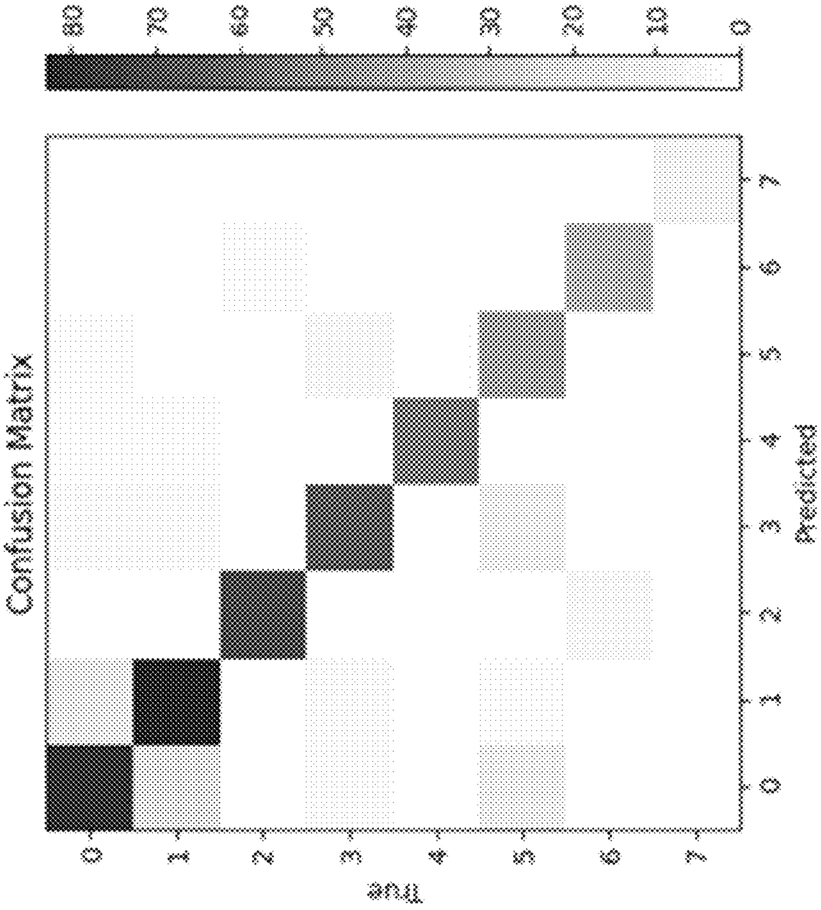
FIG. 11 is a confusion matrix for PMBC class prediction, in accordance with one or more embodiments of the present disclosure.

As proof of concept, a deep learning neural net was built to map the phenotypic space of immune cells in peripheral human blood. Peripheral human mono-nuclear cells have very well-defined phenotypic classification and are often used as testbeds to implement proof of principle or concept. Single cell ATAC-seq and RNA-seq 'omics data were obtained from PBMCs and then the corresponding phenotype was found through immune-phenotyping. Once the immune-phenotypes and the corresponding 'omics data are generated, the deep learning net is implemented. The data set consists of 2700 and 11000 PBMCs respectively which were initially clustered using UMAPS (which used a clustering algorithm and then a database annotation to annotate and label immune cells). Cells were divided into training (80%) and then testing (20%), and input to a convolution learning net with attention mechanisms. The accuracy of prediction and the confusion matrix are as shown in FIGS. 10 and 11 respectively. FIG. 10 shows the testing accuracy for each cell type in the DL net, while FIG. 11 is a confusion matrix for the prediction of each cell type.

As a proof of principle, the genotype to phenotype mapping was first captured in peripheral blood mono-nuclear cells (PBMCs) because a) the cell surface markers that define the different classes or phenotypes in the PBMCs are rather well defined and b) automatic classification of PBMCs into their respective classes from single cell RNA-seq is of considerable clinical value. This is because the current state of the art involves using an antibody cocktail of the various cell surface proteins that demark the various cell types and then to use a flow cytometry/sorting technique to progressively separate the cells out into various compartments of the peripheral blood like T cells, B cells, monocytes etc. It would be instructive also to determine if, by virtue of capturing the genotype to phenotype in the PBMCs, the scRNA-seq values could directly map to the cell surface markers and by extension the phenotype. To this end we employed an extension of the CITE-Seq technique, briefly, in CITE-Seq each cell is not only analyzed by scRNA-seq but by antibodies that bind to the cell surface proteins. So, in essence, we get both the 'omics of a given cell by the scRNA-seq but also get a quantitative readout of the number of different cell surface markers of a given cell. So not only is there a vector corresponding to the mRNA of a given cell, but there is also a vector of values for the various cell surface markers of the cell. Thus, the problem of mapping the genotype to phenotype can be reduced to the problem of mapping the scRNA-seq values to the cell surface protein markers.

A deep learning neural network based on a convolution neural network (CNN) was used with the input genes (up to 30K per cell) as the input, multiple hidden layers and the phenotypes as the output. A public database available at the 10× genomics support site, using the V3.0 version with 10,000 PBMC cells analyzed by scRNA-seq, was used to develop and test the DL-NN. The 10,000 cells and the scRNA-seq were clustered using UMAP into 8 different classes. Each class was then assigned a label from 0 to 7 and the DL-NN was trained by dividing the dataset into 90% for training and 10% for testing.

Figure 12:
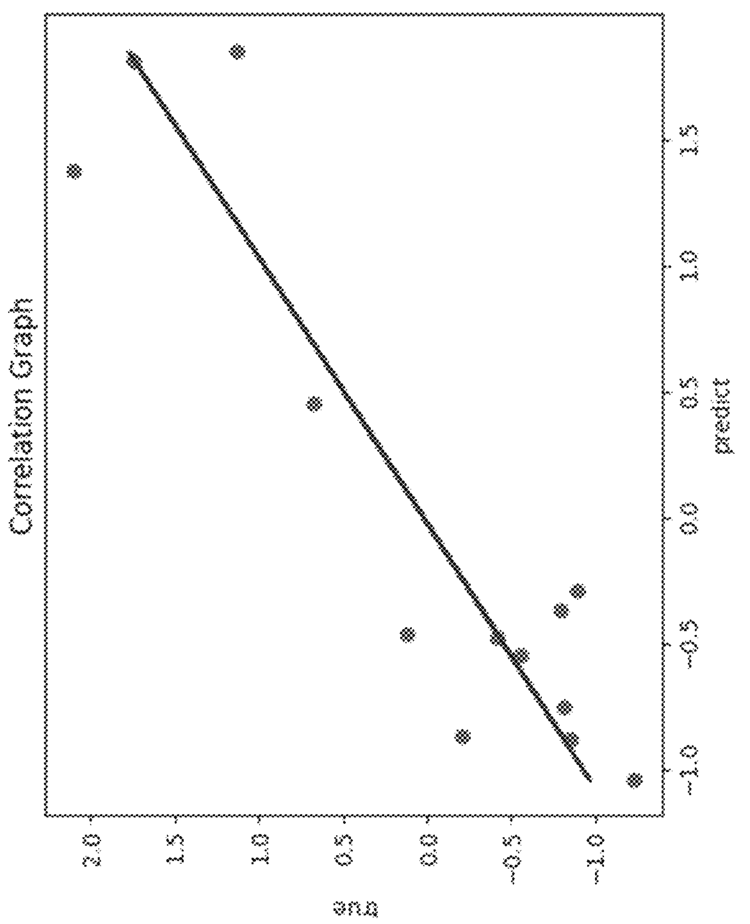
FIG. 12 is a graph illustrating the true vs. predicted value of cell surface markers from scRNA-seq data, in accordance with one or more embodiments of the present disclosure.
Figure 13:
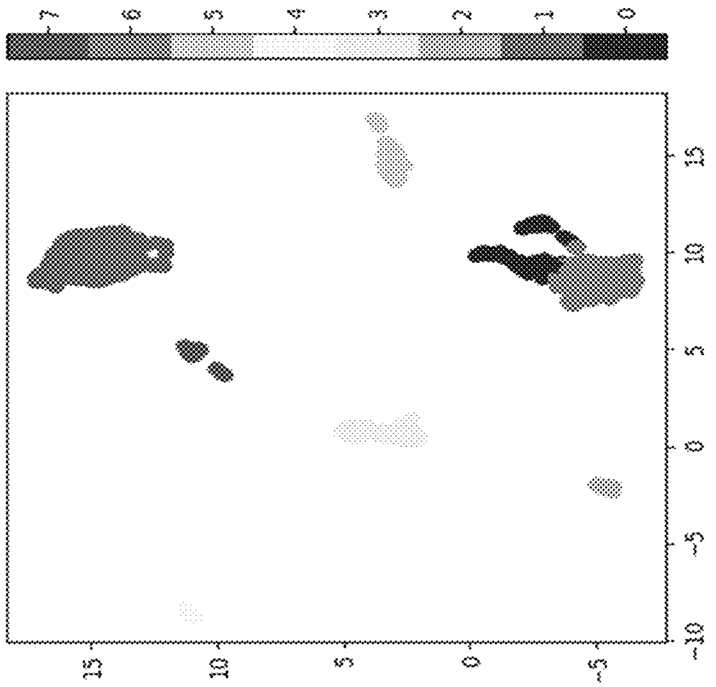
FIG. 13 is a UMAP clustering schematic for cell surface markers, in accordance with one or more embodiments of the present disclosure.
Figure 14:
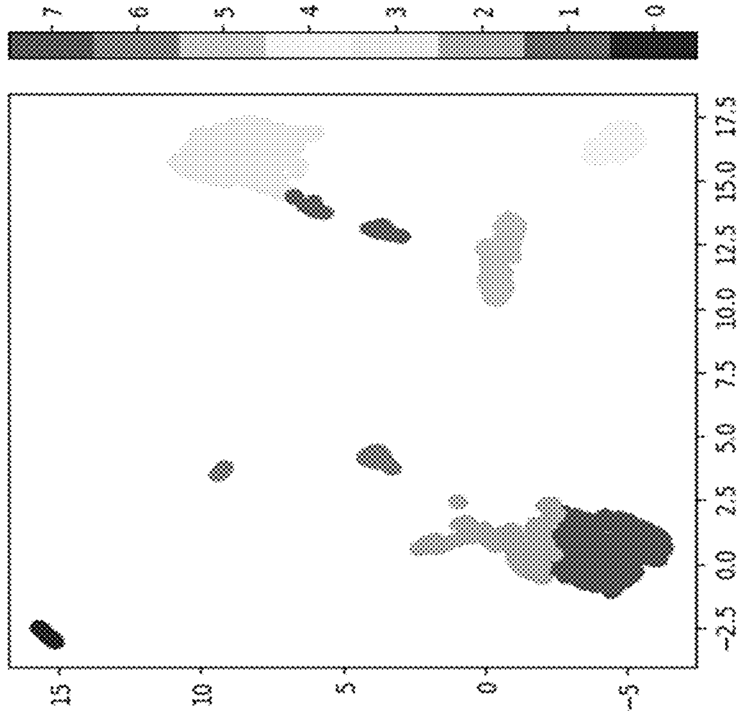
FIG. 14 is a UMAP clustering schematic for predicted cell surface markers, in accordance with one or more embodiments of the present disclosure.

The CNN accuracy for each cell in a given cluster is shown in FIG. 10 and the confusion matrix for prediction of the cell type vs. the actual cell type determined from the UMAP clustering is shown in FIG. 11. The same dataset is used to predict the cell surface marker values given the scRNA-seq input values. As before, the dataset was divided into 90% training set and 10% testing set. scRNA-seq values were applied to the DL-NN at the input with the cell surface marker values as the output and the neural network was trained to learn the association. FIG. 12 shows the predicted value and the true value of the cell surface marker in one particular cell, while FIG. 13 and FIG. 14 show the UMAP clustering of the true value of the cell surface markers and the UMAP of the predicted cell surface marker respectively for the test data set. While it does seem like there is not a one-to-one correspondence between the true value of the cell surface marker and the predicted cell surface marker from the scRNA-seq data via the DL-NN, the clustering produced by the predicted cell surface values does cluster into eight groups, thus showing that the CNN structure based DL-NN does capture aspects of the mapping from the genotype to phenotype in PBMCs. Human PBMCs purchased from commercial sources will be incubated with modified CITE-seq reagents, reagents to perform scRNA-seq plus antibodies for various cell surface markers tagged to labels and then analyzed for scRNA-seq plus cell surface markers for the same cells.

Figure 15:
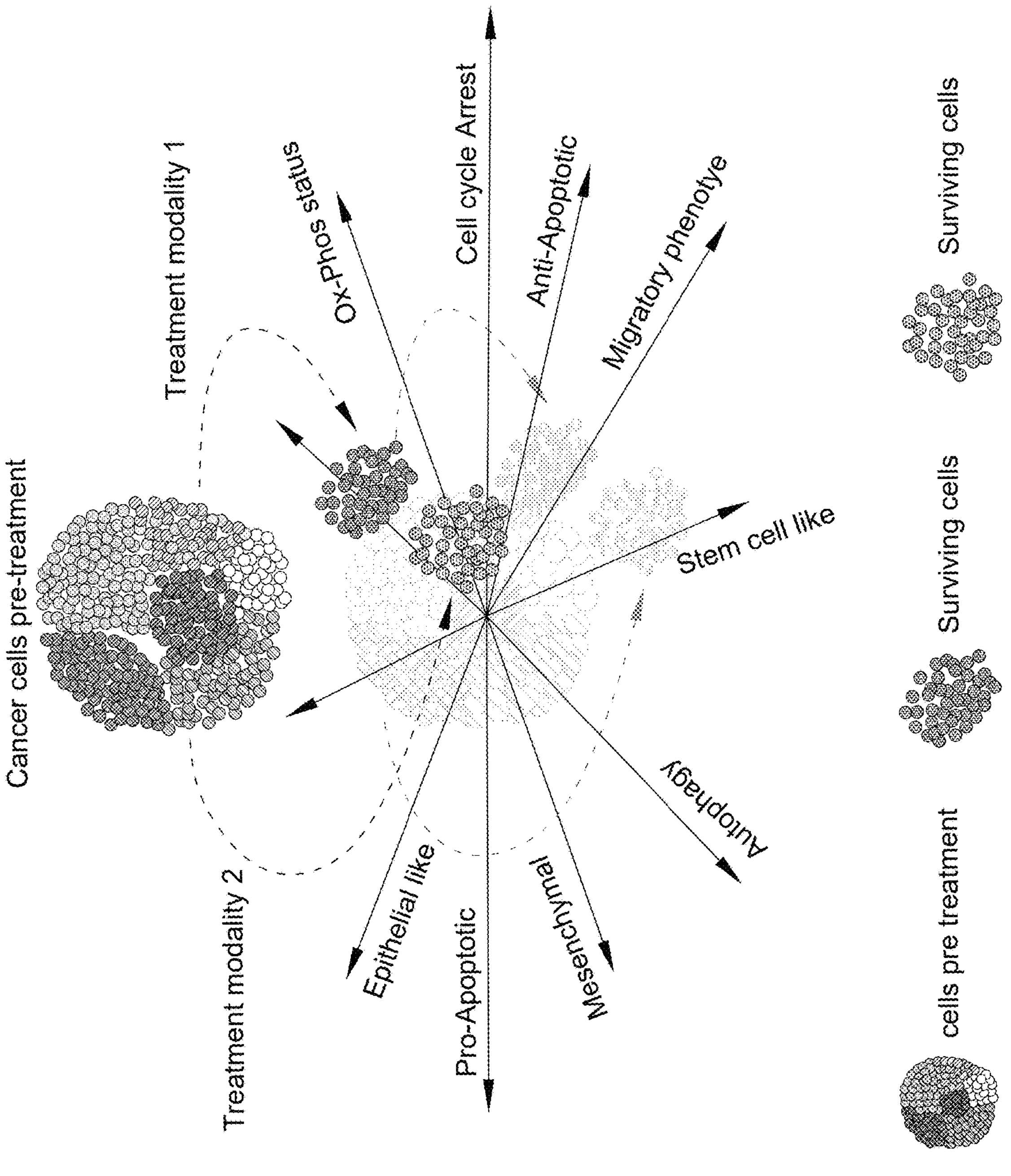
FIG. 15 is a representation of tumor cells as a cloud in multidimensional phenotypic space, in accordance with one or more embodiments of the present disclosure.

Traditional biology has always used the idea of phenotypes as measurable outcomes and readouts of biological transformation or change. Correspondingly, many of the biological assays that are designed to read and measure biological properties that could be changed by certain conditions measure phenotypes. For example, the simple MTT proliferation assay provides a quantitative readout for percentage inhibition on the application of a chemotherapeutic or a drug. While phenotypes are certainly measured with precision in biological assays, the dual need to measure the internal states and the 'omics of a given cell along with its phenotype places an unrealistic constraint. For example, the migratory speed of a cell undergoing chemotaxis could very well be estimated by simple fluorescence or phase microscopy by measuring the total distance travelled in a given amount of time but then it is a superlatively arduous task to extract the same set of cells from the substrate they are migrating on and subject them to scRNA-seq. Many phenotypic assays that are either bulk assays or require cells to be processed in a way that renders them inaccessible for sensitive assays like scRNA-seq or scATAC-seq suffer from similar limitations. CITE-seq and modifications of CITE-seq overcome some of these issues by using cell surface markers as proxy for phenotypes. Cell surface markers as surrogates for cellular phenotype and functions are also exploited by flow cytometry and sorting. State of the art CITE-seq protocols can mark up to 250 plus cell surface markers in a given cell along with the ability to either measure the gene expression through scRNA-seq or the epigenetic landscape in scATAC-seq. Cells from either a tumor cell line or a patient tumor when analyzed by both scRNA-seq and cell surface markers will enable the training of the DL-NN and provide for the representation of those cells in a multidimensional phenotypic space. The cells can then be visualized as a cloud in the multidimensional phenotypic space with various contributions towards the various phenotypes as shown in FIG. 15. Different cell lines that phenocopy certain characteristics like proliferation, migration, and stemness, for example, may be enumerated by using MCF10A, BT474 and GBM (glioblastoma) cell lines.

Figure 16:
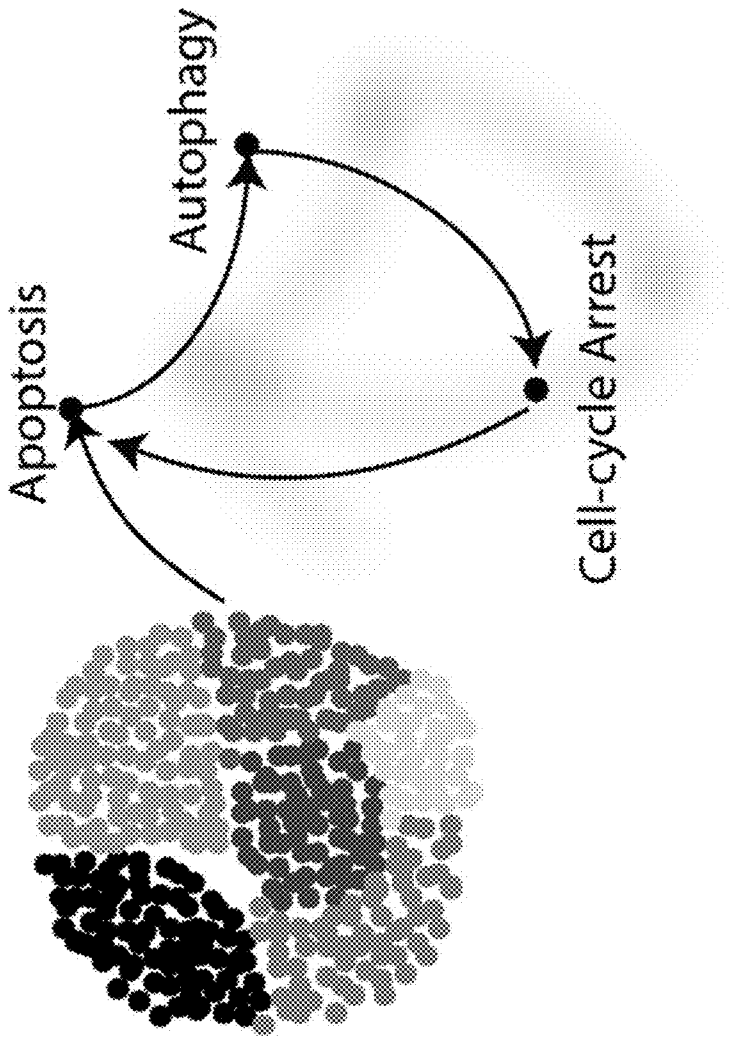
FIG. 16 is a rational combination therapy to design trajectories in phenotypic space that increase cell death, in accordance with one or more embodiments of the present disclosure.

Inhibiting the mutation causing pathway that causes the cancer, whilst killing a majority of the cells, enables the surviving cells new survival properties by virtue of rewiring of cellular networks and various feedback mechanisms. To design a rational, optimal combination therapy, the obvious requirement is that it is prevented from acquiring properties such as those that enable stress response functions, autophagy-based functions, metabolic reprogramming, stemness, etc. To help achieve this, a database is generated based on the movement of cancer cells in the phenotypic space based on the therapy. For example, when Her2+, PIK3CA mutation BT474 cells lines are treated with either Her2 inhibitors or PI3K inhibitors and the cells are analyzed before and after the application of the inhibitors, thus creating a trajectory for treatment of these cells in the multidimensional phenotypic space as shown in FIG. 16.

Figure 17:
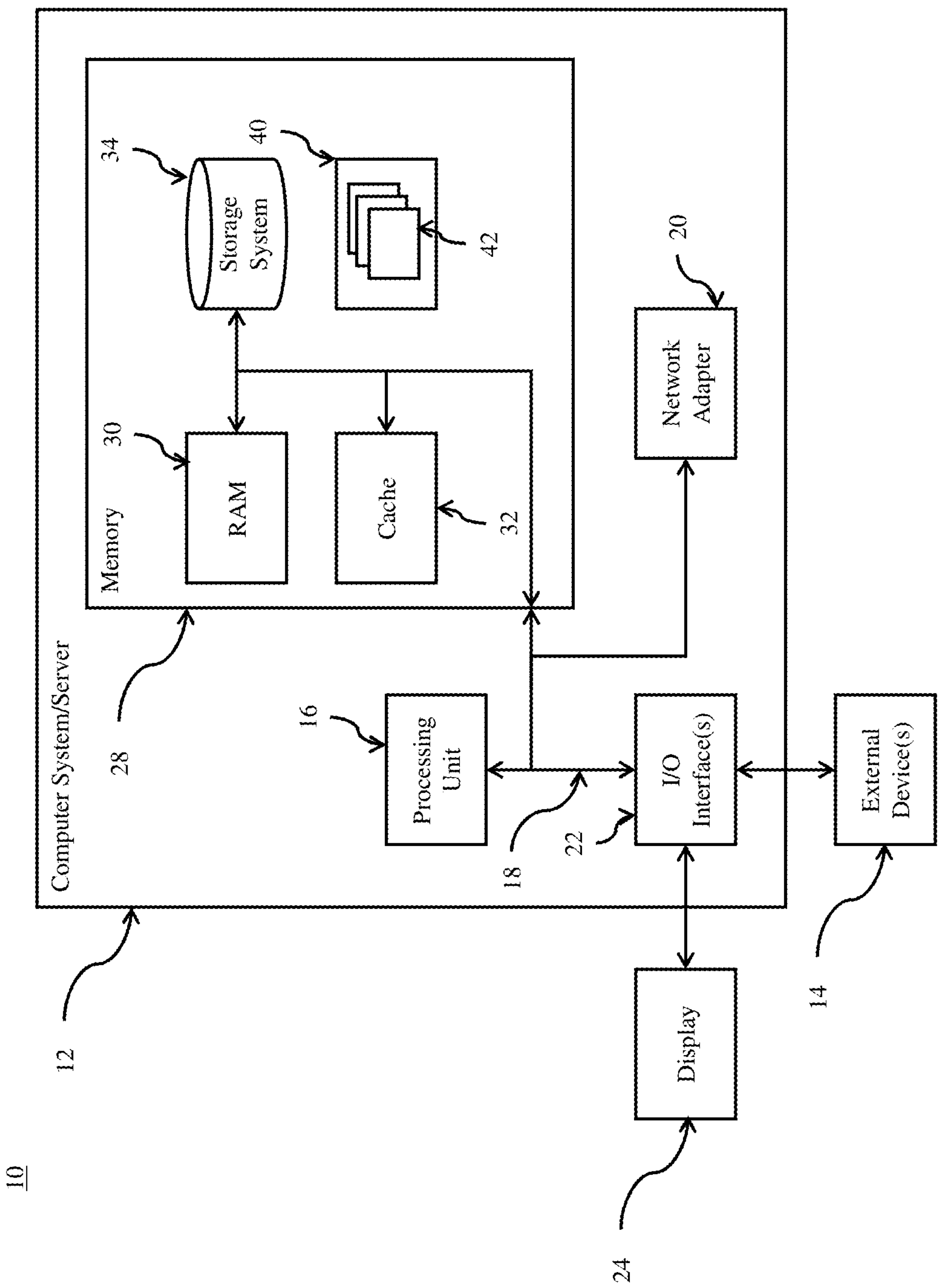
FIG. 17 is an exemplary computing node.

Referring now to FIG. 17, a schematic of an example of a computing node is shown. Computing node 10 is only one example of a suitable computing node and is not intended to suggest any limitation as to the scope of use or functionality of embodiments described herein. Regardless, computing node 10 is capable of being implemented and/or performing any of the functionality set forth hereinabove.

In computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 17, computer system/server 12 in computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, Peripheral Component Interconnect (PCI) bus, Peripheral Component Interconnect Express (PCIe), and Advanced Microcontroller Bus Architecture (AMBA).

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the disclosure.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

The present disclosure may be embodied as a system, a method, and/or a computer program product. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed:

1. A method comprising:

reading single-cell 'omics data;

providing the single-cell 'omics data to a trained artificial neural network comprising a feedforward neural network, the trained artificial neural network mapping the single-cell 'omics data to a point in a phenotypic space and wherein the trained artificial neural network is pretrained by:

reading a genetic sequence;

providing the genetic sequence to the artificial neural network;

providing a collection of phenotypic measurements to the artificial neural network, and applying the collection of phenotypic measurements to a series of cell lines to populate a dataset;

determining, from the populated dataset, an output vector representing each phenotype associated with the genetic sequence to thereby create a map of phenotypic measurements;

applying a preprocessing workflow to the single-cell 'omics data, wherein the preprocessing workflow comprising a windowing application, and wherein a short-time Fourier transformation (STFT) is applied to thereby reduce noise;

forming an image input, based on an image pool of the single-cell 'omics data;

generating an average pool of the phenotypic measurement and the phenotypic space;

predicting, based on the average pool, an associated combination of trajectories;

determining a trajectory of the point within the phenotypic space associated with at least one drug therapy; and classifying an efficacy of the at least one drug therapy based on the trajectory.

2. The method of claim 1, wherein the phenotypic space is defined by a plurality of phenotypic measurements.

3. The method of claim 1, further comprising projecting a heterogenous group of cells into the phenotypic space.

4. The method of claim 3, further comprising outputting a likelihood of survival based on a trajectory of the heterogeneous group of cells.

5. The method of claim 1, wherein the efficacy is based on one of apoptosis, migration, or autophagy.

6. The method of claim 1, further comprising optimization of the phenotypic space based on known phenotypic effect of a cell treatment.

7. The method of claim 6, further comprising outputting a set of phenotypic values characterizing the cell.

8. The method of claim 1, wherein single cell 'omics data comprises data on genomic alterations, DNA methylation sites, open chromatin sites, and mRNA or protein abundance.

9. The method of claim 1, wherein the STFT transforms windowed single-cell 'omics sequencing data into a frequency domain.

10. The method of claim 9, further comprising analyzing the frequency domain to recognize one or more patterns and/or to reduce noise.

11. The method of claim 1, wherein an output of the preprocessing workflow comprises an image pool for the single-cell 'omics sequencing data.

12. The method of claim 11, wherein the image pool comprises a spectrographic image.

13. The method of claim 1, wherein providing the single-cell 'omics sequencing data to a trained artificial neural network comprises an image input of the single-cell 'omics sequencing data.

14. A system comprising:

a computing node comprising a computer readable storage medium having program instructions embodied therewith, the program instructions executable by a processor of the computing node to cause the processor to perform a method comprising:

reading a genetic sequence including single-cell 'omics sequencing data;

providing the single-cell 'omics sequencing data to a trained artificial neural network comprising a feedforward neural network, the trained artificial neural network mapping the genetic single-cell 'omics data to a phenotypic measurement and creating a phenotypic space and wherein the trained artificial neural network is pretrained by:

reading a genetic sequence;

providing the genetic sequence to the artificial neural network;

providing a collection of phenotypic measurements to the artificial neural network, and applying the collection of phenotypic measurements to a series of cell lines to populate a dataset;

determining, from the populated dataset, an output vector representing each phenotype associated with the genetic sequence to thereby create a map of phenotypic measurements;

applying a preprocessing workflow to the single-cell 'omics data, wherein the preprocessing workflow comprising a windowing application, and wherein a short-time Fourier transformation (STFT) is applied to thereby reduce noise;

forming an image input, based on an image pool of the single-cell 'omics data;

generating an average pool of the phenotypic measurement and the phenotypic space;

predicting, based on the average pool, an associated combination of trajectories;

outputting the phenotypic measurement and the phenotypic space; and classifying a trajectory of the phenotypic measurement in the phenotypic space within a likelihood of survival.

15. A computer program product, the computer program product comprising a computer readable storage medium having program instructions embodied therewith, the program instructions executable by a processor to cause the processor to perform a method comprising:

reading a genetic sequence including single-cell 'omics sequencing data;

providing the single-cell 'omics sequencing data to a trained artificial neural network comprising a feedforward neural network, the trained artificial neural network mapping the genetic single-cell 'omics data to a phenotypic measurement and creating a phenotypic space for the genetic sequence and wherein the trained artificial neural network is pretrained by:

reading a genetic sequence;

providing the genetic sequence to the artificial neural network;

providing a collection of phenotypic measurements to the artificial neural network, and applying the collection of phenotypic measurements to a series of cell lines to populate a dataset;

determining, from the populated dataset, an output vector representing each phenotype associated with the genetic sequence to thereby create a map of phenotypic measurements;

applying a preprocessing workflow to the single-cell 'omics data, wherein the preprocessing workflow comprising a windowing application, and wherein a short-time Fourier transformation (STFT) is applied to thereby reduce noise;

forming an image input, based on an image pool of the single-cell 'omics data;

generating an average pool of the phenotypic measurement and the phenotypic space;

predicting, based on the average pool, an associated combination of trajectories:

outputting the phenotypic measurement and the phenotypic space;

classifying a trajectory of the phenotypic measurement in the phenotypic space within a likelihood of survival.

* * * * *